(12) United States Patent
Sanner et al.

(10) Patent No.: US 7,078,529 B2
(45) Date of Patent: Jul. 18, 2006

(54) IMIDAZOLE DERIVATIVES

(75) Inventors: Mark A. Sanner, Old Saybrook, CT (US); Chris J. Helal, Mystic, CT (US); Christoper B. Cooper, Lawrenceville, NJ (US); Frank S. Menniti, Mystic, CT (US); Patricia A. Seymour, Westerly, RI (US); Michael K. Ahlijanian, Mystic, CT (US); Anabella Villalobos, Niantic, CT (US); Lit-Fui Lau, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/818,855

(22) Filed: Apr. 5, 2004

(65) Prior Publication Data

US 2004/0192750 A1 Sep. 30, 2004

Related U.S. Application Data

(63) Continuation of application No. 09/919,630, filed on Jul. 31, 2001, now Pat. No. 6,756,385.

(60) Provisional application No. 60/221,724, filed on Jul. 31, 2000, provisional application No. 60/228,394, filed on Aug. 28, 2000, provisional application No. 60/229,437, filed on Aug. 31, 2000.

(51) Int. Cl.
C07D 233/88 (2006.01)
(52) U.S. Cl. .................................. 548/326.5; 514/398
(58) Field of Classification Search ............. 548/326.5; 514/398
See application file for complete search history.

(56) References Cited

OTHER PUBLICATIONS

Nielsen et al., Tetrahedron, vol. 38, No. 10, pp. 1435-1441, (1982).*
Database CAS ONLINE on STN, Chem. Abstr., Accession No. 2000:903927, Suwinski et al. Polish Journal of Applied Chemistry (2000), 44(1), pp. 31-35, (2000), abstract.*
Cancer and Metastasis Reviews (1998), 17(1), 91-106.*
Science (1999), vol. 286, 531-537.*
FDA mulls drug to slow late-stage Alzheimer's [online], [retrieved on Sep. 23, 2003]. Retrieved from the Internet,URL;http://www.cnn.com/2003/HEALTH/conditions/09/24/alzheimers.drug.ap/index.html>.*
Database CAS ONLINE on STN, Chem. Abstr., Accession No. 1987:102189, Kasek et al., Zeitschrift fuer Chemie (1986), 26(4), 136, abstract.*

* cited by examiner

Primary Examiner—Kamal A. Saeed
Assistant Examiner—Rebecca Anderson
(74) Attorney, Agent, or Firm—Steve T. Zelson; James A. Jubinsky

(57) ABSTRACT

The invention provides compounds of formula 1

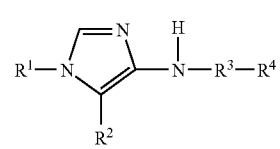

wherein $R^1$, $R^2$, $R^3$, and $R^4$ are as defined, and their pharmaceutically acceptable salts. Compounds of formula 1 are indicated to have activity inhibiting cdk5, cdk2, and GSK-3. Pharmaceutical compositions and methods comprising compounds of formula 1 for treating and preventing diseases and conditions comprising abnormal cell growth, such as cancer, and neurodegenerative diseases and conditions and those affected by dopamine neurotransmission. Also described are pharmaceutical compositions and methods comprising compounds of formula 1 for treating male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency.

13 Claims, No Drawings

IMIDAZOLE DERIVATIVES

This application is a continuation application of U.S. Ser. No. 09/919,630, filed on Jul. 31, 2001 now U.S. Pat. No. 6,756,385 which claims priority under 35 U.S.C. 119(e) of U.S. Application Ser. Nos. 60/221,724, filed on Jul. 31, 2000; 60/228,394, filed on Aug. 28, 2000; and 60/229,437, filed on Aug. 31, 2000. The entire disclosure of the prior application is hereby incorporated by reference.

FIELD OF THE INVENTION

The subject invention relates to imidazole derivatives, pharmaceutical compositions comprising such derivatives and methods of using such derivatives to treat abnormal cell growth and certain diseases and conditions of the central nervous system. The compounds of the present invention act as inhibitors of cyclin-dependent protein kinase enzymes cdk5 (cyclin-dependent protein kinase 5) and cdk2 (cyclin-dependent protein kinase 2). The compounds of the present invention also are inhibitors of the enzyme GSK-3 (glygocen synthase kinase-3) enzyme.

BACKGROUND OF THE INVENTION

The serine/threonine kinase cdk5 along with its cofactor p25 (or the longer cofactor, p35) has been linked to neurodegenerative disorders, and inhibitors of cdk5/p25 (or cdk5/p35) are therefore useful for the treatment of neurodegenerative disorders such as Alzheimer's disease, Parkinson's disease, stroke, or Huntington's disease. Treatment of such neurodegenerative disorders using cdk5 inhibitors is supported by the finding that cdk5 is involved in the phosphorylation of tau protein (*J. Biochem*, 117, 741–749 (1995)). cdk5 also phosphorylates Dopamine and Cyclic AMP-Regulated Phosphorprotein (DARPP-32) at threonine 75 and is thus indicated in having a role in dopaminergic neurotransmission (*Nature*, 402, 669–671 (1999)).

The serine/threonine kinase cdk2 is essential for normal cell cycling and plays a critical role in disorders arising from abnormal cell cycling, a common characteristic of many oncological disorders. Inhibitors of cdk2 are therefore useful for the treatment of various types of cancer and other diseases or conditions related to abnormal cell growth (Meijer, et al., *Properties and Potential-applications of Chemical Inhibitors of Cyclin-dependent Kinsases, Pharmacology & therapeutics*, 82 (2–3), 279–284 (1999); Sausville, et al., *Cyclin-dependent Kinases: Initial Approaches to Exploit a Novel Therapeutic Target, Pharmacology & therapeutics* 82 (2–3) 285–292 (1999)).

GSK-3 is a serine/threonine protein kinase. It is one of several protein kinases which phosphorylate glycogen synthase (Embi, et al., *Eur. J. Biochem.* 107:519–527 (1980); Hemmings, et al., *Eur. J. Biochem.* 119:443–451 (1982)). GSK-3 exists in two isoforms, α and β, in vertebrates, reported as having a monomeric structure of 49 kD and 47 kD respectively. Both isoforms phosphorylate muscle glycogen synthase (Cross, et al., *Biochemical Journal* 303: 21–26 (1994)). The amino acid identity among GSK-3 species homologs has been indicated to be in excess of 98% within the catalytic domain (Plyte, et al., *Biochim. Biophys. Acta* 1114:147–162) (1992)). Due to a remarkably high degree of conservation across the phylogenetic spectrum, a fundamental role of GSK-3 in cellular processes is suggested.

GSK-3 has been implicated in numerous different disease states and conditions. For example, Chen, et al, *Diabetes* 43: 1234–1241 (1994) have suggested that an increase in GSK-3 activity can be important in Type 2 diabetes. Increased GSK-3 expression in diabetic muscle is also though to contribute to the impaired glycogen synthase activity and skeletal muscle insulin resistance present in Type 2 diabetes (Nikoulina, et al., *Diabetes* 49: 263–271 (2000)). Also, a higher activity of a type 1 protein phosphatase measured in immotile sperm was attributed to higher GSK-3 activity and was indicated as responsible for holding the sperm motility in check (Vijayaraghavan, et al. *Biology of Reproduction* 54: 709–718 (1996)). Vijayaraghavan et al. indicate that such results suggest a biochemical basis for the development and regulation of sperm motility and a possible physiological role for a protein phosphatase 1/inhibitor 2/GSK-3 system. GSK-3 activity has also been associated with Alzheimer's disease and mood disorders such as bipolar disorder (WO 97/41854). Among other conditions, GSK-3 has furthermore been implicated in hair loss, schizophrenia, and neurodegeneration, including both chronic neurodegenerative diseases (such as Alzheimer's, supra) and neurotrauma, for example stroke, traumatic brain injury, and spinal cord trauma.

SUMMARY OF THE INVENTION

This invention provides compounds of the formula

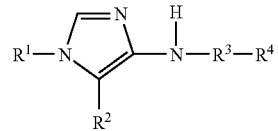

wherein $R^1$ is a straight chain or branched $(C_1-C_8)$alkyl, a straight chain or branched $(C_2-C_8)$alkenyl, a straight chain or branched $(C_2-C_8)$alkynyl, $(C_3-C_8)$cycloalkyl, $(C_4-C_8)$ cycloalkenyl, (3–8 membered) heterocycloalkyl, $(C_5-C_{11})$ bicycloalkyl, $(C_7-C_{11})$bicycloalkenyl, (5–11 membered) heterobicycloalkyl, $(C_6-C_{14})$ aryl, or (5–14 membered) heteroaryl; and wherein $R^1$ is optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2$ $R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, —O—$S(=O)_2R^7$, —$N_3$ and $R^7$.

$R^2$ is H, F, $CH_3$, CN, or $C(=O)OR^7$;

$R^3$ is —$C(=O)NR^9$—, —$C(=O)O$—, —$C(=O)$ $(CR^{10}R^{11})_n$—, or —$(CR^{10}R^{11})_n$—;

$R^4$ is a straight chain or a branched $(C_1-C_8)$alkyl, a straight chain or a branched $(C_2-C_8)$alkenyl, a straight chain or branched $(C_2-C_8$ alkynyl), $(C_3-C_8)$cycloalkyl, $(C_4-C_8)$ cycloalkenyl, (3–8 membered) heterocycloalkyl, $(C_5-C_{11})$ bicycloalkyl, $(C_7-C_{11})$bicycloalkenyl, (5–11 membered) heterobicycloalkyl, $(C_6-C_{14})$aryl, or (5–14 membered) heteroaryl; and wherein $R^4$ is optionally substituted with from one to three substitutents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2$ $R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, or $R^7$;

each $R^7$, $R^8$, and $R^9$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^7$, $R^8$, and $R^9$ are each independently optionally substituted with from one to six substituents independently selected from F, Cl, Br, I, $NO_2$, —CN, —$CF_3$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, $OC(=O)R^{10}$, —$OC(=O)OR^{10}$, —$OC(=O)NR^{10}R^{11}$, —$OC(=O)SR^{10}$, —$SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}R^{11}$, and $R^{10}$;

or, when $R^7$ and $R^8$ are as in $NR^7R^8$, they may instead optionally be connected to form with the nitrogen of $NR^7R^8$ to which they are attached a heterocycloalkyl moiety of from three to seven ring members, said heterocycloalkyl moiety optionally comprising one or two further heteroatoms independently selected from N, O, and S;

each $R^{10}$, $R^{11}$, and $R^{12}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{10}$, $R^{11}$, and $R^{12}$ are each independently optionally substituted with from one to six substituents independently selected from F, Cl, Br, I, $NO_2$, —CN, —$CF_3$, —$NR^{13}R^{14}$, —$NR^{13}C(=O)R^{14}$, —$NR^{13}C(=O)OR^{14}$, —$NR^{13}C(=O)NR^{14}R^{15}$, —$NR^{13}S(=O)_2R^{14}$, —$NR^{13}S(=O)_2NR^{14}R^{15}$, —$OR^{13}$, —$OC(=O)R^{13}$, —$OC(=O)OR^{13}$, —$OC(=O)NR^{13}R^{14}$, —$OC(=O)SR^{13}$, —$SR^{13}$, —$S(=O)R^{13}$, —$S(=O)_2R^{13}$, —$S(=O)_2NR^{13}R^{14}$, —$C(=O)R^{13}$, —$C(=O)OR^{13}$, —$C(=O)NR^{13}R^{14}$, and $R^{13}$;

each $R^{13}$, $R^{14}$, and $R^{15}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl, wherein $R^{13}$, $R^{14}$, and $R^{15}$ are each independently optionally substituted with from one to six substituents independently selected from F, Cl, Br, I, $NO_2$, —CN, —$CF_3$, —$NR^{16}R^{17}$, —$NR^{16}C(=O)R^{17}$, —$NR^{16}C(=O)OR^{17}$, —$NR^{16}C(=O)NR^{17}R^{18}$, —$NR^{16}S(=O)_2R^{17}$, —$NR^{16}S(=O)_2NR^{17}R^{18}$, —$OR^{16}$, —$OC(=O)R^{16}$, —$OC(=O)OR^{16}$, —$OC(=O)NR^{16}R^{17}$, —$OC(=O)SR^{16}$, —$SR^{16}$, —$S(=O)R^{16}$, —$S(=O)_2R^{16}$, —$S(=O)_2NR^{16}R^{17}$, —$C(=O)R^{16}$, —$C(=O)OR^{16}$, —$C(=O)NR^{16}R^{17}$, and $R^{16}$, each $R^{16}$, $R^{17}$, and $R^{18}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, (3–8 membered) heterocycloalkyl, ($C_5$–$C_{11}$)bicycloalkyl, ($C_7$–$C_{11}$)bicycloalkenyl, (5–11 membered) heterobicycloalkyl, ($C_6$–$C_{14}$)aryl, and (5–14 membered) heteroaryl;

n is 0, 1, 2, or 3;

wherein $R^{10}$ and $R^{11}$ in —$C(=O)(CR^{10}R^{11})_n$— and —$(CR^{10}R^{11})_n$— are for each iteration of n defined independently as recited above;

and pharmaceutically acceptable salts thereof.

Compounds of formula 1 of the invention are inhibitors of serine/threonine kinases, especially cyclin-dependent kinases such as cdk5 and cdk2, and are useful for the treatment of neurodegenerative disorders and other CNS disorders, and of abnormal cell growth, including cancer. The compounds of formula 1 are particularly useful in inhibiting cdk5. The compounds of formula 1 are also useful as inhibitors of GSK-3.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings, wherein said rings share one or two carbon atoms. For purposes of the present invention, and unless otherwise indicated, bicycloalkyl groups include spiro groups and fused ring groups. Examples of bicycloalkyl groups include, but are not limited to, bicyclo-[3.1.0]-hexyl, norbornyl, spiro[4.5]decyl, spiro[4.4]nonyl, spiro[4.3]octyl, and spiro[4.2]heptyl. "Cycloalkenyl" and "bicycloalkenyl" refer to non-aromatic carbocyclic cycloalkyl and bicycloalkyl moieties as defined above, except comprising one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclobutenyl, and a non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl, and norcamphoryl.

The term "aryl", as used herein, unless otherwise indicated, includes an organic radical derived from an aromatic hydrocarbon by removal of one hydrogen, such as phenyl, naphthyl, indenyl, and fluorenyl.

The terms "heterocyclic", "heterocycloalkyl", and like terms, as used herein, refer to non-aromatic cyclic groups containing one or more heteroatoms, prefereably from one to four heteroatoms, each selected from O, S and N. "Heterobicycloalkyl" groups are non-aromatic two-ringed cyclic groups, wherein said rings share one or two atoms, and wherein at least one of the rings contains a heteroatom (O, S, or N). Heterobicycloalkyl groups for purposes of the present invention, and unless otherwise indicated, include spiro groups and fused ring groups. In one embodiment, each ring in the heterobicycloalkyl contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

"Heteroaryl", as used herein, refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

In one embodiment, this invention provides compounds of formula 1, wherein $R^3$ is —C(=O)$NR^9$— or —C(=O)($CR^{10}R^{11}$)$_n$—. In another embodiment, $R^{10}$ and $R^{11}$ of —C(=O)($CR^{10}R^{11}$)$_n$— are at each iteration in both hydrogen. In another embodiment, $R^9$ of —C(=O)$NR^9$— is hydrogen. In another embodiment, $R^3$ is —C(=O)$NR^9$— or —C(=O)($CR^{10}R^{11}$)$_n$— and $R^2$ is hydrogen.

In another embodiment of the invention, a compound of formula 1 is provided wherein $R^1$ is optionally substituted ($C_3$–$C_8$)cycloalkyl or optionally substituted ($C_5$–$C_{11}$) bicycloalkyl. Preferred embodiments are wherein $R^1$ is cyclopropyl, cyclobutyl, cyclopentyl, cyclohexyl, or norbornyl, each optionally substituted as recited above (i.e. optionally with from one to six substituents $R^5$ independently selected from F, Cl, Br, I, nitro, cyano, —$CF_3$, —$NR^7R^8$, —$NR^7C$(=O)$R^8$, —$NR^7C$(=O)$OR^8$, —$NR^7C$(=O)$NR^8R^9$, —$NR^7S$(=O)$_2R^8$, —$NR^7S$(=O)$_2NR^8R^9$, —$OR^7$, —OC(=O)$R^7$, —OC(=O)$OR^7$, —C(=O)$OR^7$, —C(=O)$R^7$, —C(=O)$NR^7R^8$, —OC(=O)$NR^7R^8$, —OC(=O)$SR^7$, —$SR^7$, —S(=O)$R^7$, —S(=O)$_2R^7$, —S(=O)$_2NR^7R^8$, and $R^7$). In a more preferred embodiment, $R^1$ is ($C_3$–$C_8$)cycloalkyl or optionally substituted ($C_5$–$C_{11}$) bicycloalkyl, for example cyclopropyl, cyclobutyl, cyclopentyl, cyclohexyl, or norbornyl, and is optionally substituted with from one to three substituents independently selected from F, Cl, Br, I, nitro, cyano, —$CF_3$, —$NR^7R^8$, —$NR^7C$(=O)$R^8$, —$OR^7$, —C(=O)$OR^7$, —C(=O)$R^7$, and $R^7$. More preferably, $R^1$ is ($C_3$–$C_8$)cycloalkyl or optionally substituted ($C_5$–$C_{11}$) bicycloalkyl, for example cyclopropyl, cyclobutyl, cyclopentyl, cyclohexyl, or norbornyl, and $R^1$ is substituted with —$NR^7C$(=O)$R^8$, ($C_6$–$C_{14}$)aryl, (3–8 membered) heterocycloalkyl, or (5–14 membered) heteroaryl, and wherein said aryl, heterocycloalkyl, and heteroaryl are each optionally substituted with from one to six substituents independently selected from F, Cl, Br, I, $NO_2$, —CN, —$CF_3$, —$NR^{10}R^{11}$, —$NR^{10}C$(=O)$R^{11}$, —$NR^{10}C$(=O)$OR^{11}$, —$NR^{10}C$(=O)$NR^{11}R^{12}$, —$NR^{10}S$(=O)$_2R^{11}$, —$NR^{10}S$(=O)$_2NR^{11}R^{12}$, —$OR^{10}$, —OC(=O)$R^{10}$, —OC(=O)$OR^{10}$, —OC(=O)$NR^{10}R^{11}$, —OC(=O)$SR^{10}$, —$SR^{10}$, —S(=O)$R^{10}$, —S(=O)$_2R^{10}$, —S(=O)$_2NR^{10}R^{11}$, —C(=O)$R^{10}$, —C(=O)$OR^{10}$, —C(=O)$NR^{10}R^{11}$, and $R^{10}$. In another embodiment of the invention, $R^1$ is bicyclo-[3.1.0]-hexyl and is optionally substituted as recited above (i.e. optionally substituted with from one to six substituents $R^5$ independently selected from F, Cl, Br, I, nitro, cyano, —$CF_3$, —$NR^7R^8$, —$NR^7C$(=O)$R^8$, —$NR^7C$(=O)$OR^8$, —$NR^7C$(=O)$NR^8R^9$, —$NR^7S$(=O)$_2R^8$, —$NR^7S$(=O)$_2NR^8R^9$, —$OR^7$, —OC(=O)$R^7$, —OC(=O)$OR^7$, —C(=O)$OR^7$, —C(=O)$R^7$, —C(=O)$NR^7R^8$, —OC(=O)$NR^7R^8$, —OC(=O)$SR^7$, —$SR^7$, —S(=O)$R^7$, —S(=O)$_2R^7$, —S(=O)$_2NR^7R^8$, and $R^7$).

In another embodiment of the invention, a compound of formula 1 is provided wherein $R^1$ is optionally substituted straight chain or branched ($C_1$–$C_8$)alkyl or optionally substituted straight chain or branched ($C_2$–$C_8$)alkenyl.

In another embodiment of the invention, compounds of formula 1 are provided, but wherein $R^2$ is hydrogen. In a further embodiment, $R^2$ is hydrogen, and $R^1$ is as subdefined in the preceding paragraphs.

In another embodiment, this invention provides a compound of formula 1 wherein $R^4$ is ($C_6$–$C_{14}$)aryl or (5–14 membered) heteroaryl, each optionally substituted. In a preferred embodiment, $R^4$ is optionally substituted phenyl or optionally substituted pyridyl. In another preferred embodiment, $R^4$ is naphthyl, quinolyl, or isoquinolyl, each optionally substituted. In another embodiment, $R^4$ is napthyl, quinolyl, or isoquinolyl, and is unsubstituted.

In another embodiment, compounds of formula 1 are provided, wherein $R^2$ is specifically hydrogen, and $R^4$ is as subdefined in the preceding paragraph.

Examples of preferred compounds of formula 1 are:
N-(1-cyclobutyl-1H-imidazol-4-yl)-2-quinolin-6-yl-acetamide;
N-(1-cyclopentyl-1H-imidazol-4-yl)-2-(4-methoxy-phenyl)-acetamide;
N-[1-(cis-3-phenyl-cyclobutyl)-1H-imidazol-4-yl]-2-quinolin-6-yl-acetamide;
(1-cyclobutyl-1H-imidazol-4-yl)-carbamic acid phenyl ester;
1-(1-cyclobutyl-1H-imidazol-4-yl)-3-isoquinolin-5-yl-urea;
N-[1-(cis-3-amino-cyclobutyl)-1H-imidazol-4-yl]-2-naphthalen-1-yl-acetamide;
6-methyl-pyridine-2-carboxylic acid {cis-3-[4-(2-naphthalen-1-yl-acetylamino)-imidazol-1-yl]-cyclobutyl}-amide;
1H-imidazole-4-carboxylic acid {cis-3-[4-(2-naphthalen-1-yl-acetylamino)-imidazol-1-yl]-cyclobutyl}-amide;
6-hydroxy-pyridine-2-carboxylic acid {cis-3-[4-(2-naphthalen-1-yl-acetylamino)-imidazol-1-yl]-cyclobutyl}-amide;
3-methyl-pyridine-2-carboxylic acid {cis-3-[4-(2-naphthalen-1-yl-acetylamino)-imidazol-1-yl]-cyclobutyl}-amide;
2-pyridin-3-yl-thiazole-4-carboxylic acid {cis-3-[4-(2-naphthalen-1-yl-acetylamino)-imidazol-1-yl]-cyclobutyl}-amide;
6-{cis-3-[4-(2-naphthalen-1-yl-acetylamino)-imidazol-1-yl]-cyclobutylcarbamoyl}-nicotinic acid methyl ester;

pyrazine-2-carboxylic acid {cis-3-[4-(2-naphthalen-1-yl-acetylamino)-imidazol-1-yl]-cyclobutyl}-amide;
N-{cis-3-[4-(2-naphthalen-1-yl-acetylamino)-imidazol-1-yl]-cyclobutyl}-benzamide;
5-methyl-pyrazine-2-carboxylic acid {cis-3-[4-(2-naphthalen-1-yl-acetylamino)-imidazol-1-yl]-cyclobutyl}-amide;
N-{cis-3-[4-(2-naphthalen-1-yl-acetylamino)-imidazol-1-yl]-cyclobutyl}-isobutyramide;
6-chloro-pyridine-2-carboxylic acid {cis-3-[4-(2-naphthalen-1-yl-acetylamino)-imidazol-1-yl]-cyclobutyl}-amide;
quinoline-2-carboxylic acid {cis-3-[4-(2-naphthalen-1-yl-acetylamino)-imidazol-1-yl]-cyclobutyl}-amide;
1H-pyrrole-2-carboxylic acid {cis-3-[4-(2-naphthalen-1-yl-acetylamino)-imidazol-1-yl]-cyclobutyl}-amide;
N{cis-3-[4-(2-naphthalen-1-yl-acetylamino)-imidazol-1-yl]-cyclobutyl}-2-m-tolyl-acetamide;
pyridine-2-carboxylic acid {cis-3-[4-(2-naphthalen-1-yl-acetylamino)-imidazol-1-yl]-cyclobutyl}-amide;
2-(3-hydroxy-phenyl)-N-{cis-3-[4-(2-naphthalen-1-yl-acetylamino)-imidazol-1-yl]-cyclobutyl}-acetamide;
piperidine-4-carboxylic acid {cis-3-[4-(2-naphthalen-1-yl-acetylamino)-imidazol-1-yl]-cyclobutyl}-amide hydrochloride;
N-[1-(cis-3-acetylamino-cyclobutyl )-1H-imidazol-4-yl]-2-naphthalen-2-yl-acetamide;
N-{cis-3-[4-(2-isoquinolin-5-yl-acetylamino)-imidazol-1-yl]-cyclobutyl}-benzamide; and
pyridine-2-carboxylic acid {cis-3-[4-(2-isoquinolin-5-yl-acetylamino)-imidazol-1-yl]-cyclobutyl}-amide; and pharmaceutically acceptable salts of the foregoing compounds.

Examples of other specific compound of the invention of formula 1 are:
cis-N-(1-bicyclo[3.1.0]hex-3-yl-1H-imidazol-4-yl)-2-quinolin-6-yl-acetamide;
cis-N-{1-[trans-6-(pyridine-2-carbonyl)-bicyclo[3.1.0]hex-3-yl]-1H-imidazol-4-yl}-2-quinolin-6-yl-acetamide;
N-{1-[cis-3-(2-methoxy-phenyl)-cyclobutyl]-1H-imidazol-4-yl}-2-quinolin-6-yl-acetamide;
N-{1-[cis-3-(2-fluoro-phenyl)-cyclobutyl]-1H-imidazol-4-yl}-2-quinolin-6-yl-acetamide;
N-{1-[cis-3-(4-methoxy-phenyl)-cyclobutyl]-1H-imidazol-4-yl}-2-quinolin-6-yl-acetamide;
2-quinolin-6-yl-N-[1-(cis-3-p-tolyl-cyclobutyl)-1H-imidazol-4-yl]-acetamide;
N-{1-[cis-3-(2-ethoxy-phenyl)-cyclobutyl]-1H-imidazol-4-yl}-2-quinolin-6-yl-acetamide;
N-{1-[cis-3-(3-methoxy-phenyl)-cyclobutyl]-1H-imidazol-4-yl}-2-quinolin-6-yl-acetamide; and pharmaceutically acceptable salts of the foregoing compounds.

Other examples of specific compounds of formula 1 are:
N-{1-[3-(2-hydroxy-phenyl)-cyclobutyl]-1H-imidazol-4-yl}-2-(4-methoxy-phenyl)-acetamide;
N-{1-[3-(3-hydroxy-phenyl)-cyclobutyl]-1H-imidazol-4-yl}-2-(4-methoxy-phenyl)-acetamide;
N-{1-[3-(2-amino-phenyl)-cyclobutyl]-1H-imidazol-4-yl}-2-(4-methoxy-phenyl)-acetamide;
N-{1-[3-(3-amino-phenyl)-cyclobutyl]-1H-imidazol-4-yl}-2-(4-methoxy-phenyl)-acetamide;
N-{1-[3-(3-aminomethyl-phenyl)-cyclobutyl]-1H-imidazol-4-yl}-2-(4-methoxy-phenyl)-acetamide;
N-{1-[3-(3-dimethylaminomethyl-phenyl)-cyclobutyl]-1H-imidazol-4-yl}-2-(4-methoxy-phenyl)-acetamide; and
2-(4-methoxy-phenyl)-N-{1-[3-(1-methyl-1H-pyrazol-3-yl)-cyclobutyl]-1H-imidazol-4-yl}-acetamide;

and pharmaceutically acceptable salts of the foregoing compounds.

Salts of compounds of formula 1 can be obtained by forming salts with any acidic or basic group present on a compound of formula 1. Examples of pharmaceutically acceptable salts of the compounds of formula 1 are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium.

The compounds of formula 1 may have optical centers and therefore may occur in different enantiomeric and other stereoisomeric configurations. The invention includes all enantiomers, diastereomers, and other stereoisomers of such compounds of formula 1, as well as racemic and other mixtures thereof.

The subject invention also includes isotopically-labeled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula 1 of this invention can generally be prepared by carrying out the procedures disclosed in the Schemes and/or in the Examples below, by substituting a readily available isotopically labeled reagent for a non-isotopically labeled reagent.

This invention also provides a pharmaceutical composition for treating a disease or condition comprising abnormal cell growth in a mammal comprising a compound of formula 1 in an amount effective in inhibiting abnormal cell growth, and a pharmaceutically acceptable carrier.

This invention also provides a pharmaceutical composition for treating a diseases or condition comprising abnormal cell growth in a mammal comprising a compound of formula 1 in an amount effective to inhibit cdk2 activity, and a pharmaceutically acceptable carrier.

This invention also provides a method for treating a disease or condition comprising abnormal cell growth in a mammal comprising administering to the mammal a compound of formula 1 in an amount effective in inhibiting abnormal cell growth.

This invention also provides a method for treating a diseases or condition comprising abnormal cell growth in a mammal comprising administering to the mammal a compound of formula 1 in an amount effective to inhibit cdk2 activity.

In a pharmaceutical composition or method of this invention for treating a disease or condition comprising abnormal cell growth, the disease or condition comprising abnormal cell growth is in one embodiment cancer. The cancer may be a carcinoma, for example carcinoma of the bladder, breast, colon, kidney, liver, lung, for example small cell lung cancer, esophagus, gall bladder, ovary, pancreas, stomach, cervix, thyroid, prostate, or skin, for example squamous cell carcinoma; a hematopoietic tumor of lymphoid lineage, for example leukemia, acute lymphocytic leukemia, B-cell lymphoma, T-cell lymphoma, Hodgkins lymphoma, non-Hodgkins lymphoma, hairy cell lymphoma, or Burkett's lymphoma; a hematopoietic tumor of myeloid lineage, for example acute and chronic myelogenous leukemias, myelodysplastic syndrome, or promyelocytic leukemia; a tumor of mesenchymal origin, for example fibrosarcoma or rhabdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; or Kaposi's sarcoma.

In another embodiment, the disease or condition comprising abnormal cell growth is benign. Such diseases and conditions include benign prostate hyperplasia, familial adenomatosis polyposis, neuro-fibromatosis, atherosclerosis, pulmonary fibrosis, arthritis, psoriasis, glomerulonephritis, restenosis, hypertrophic scar formation, inflammatory bowel disease, transplantation rejection, fungal infection, and endotoxic shock.

This invention also provides a pharmaceutical composition for treating a neurodegenerative disease or condition in a mammal comprising a compound of formula 1 in an amount effective in treating said disease or condition, and a pharmaceutically acceptable carrier.

This invention also provides a pharmaceutical composition for treating a neurodegenerative disease or condition in a mammal comprising a compound of formula 1 in an amount effective in inhibiting cdk5 activity, and a pharmaceutically acceptable carrier.

This invention also provides a method for treating a neurodegenerative disease or condition in a mammal comprising administering to the mammal a compound of formula 1 in an amount effective in inhibiting cdk5 activity.

This invention also provides a method for treating a neurodegenerative disease or condition in a mammal comprising administering to the mammal a compound of formula 1 in an amount effective in treating said disease or condition.

In one embodiment of the invention, the neurodegenerative disease or condition which is treated is selected from Huntington's disease, stroke, spinal cord trauma, traumatic brain injury, multiinfarct dementia, epilepsy, amyotrophic lateral sclerosis, pain, viral induced dementia for example AIDS induced dementia, neurodegeneration associated with bacterial infection, migraine, hypoglycemia, urinary incontinece, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis.

This invention also provides a pharmaceutical composition for treating a disease or condition the treatment of which can be effected or facilitated by altering dopamine mediated neurotransmission in a mammal comprising a cdk5 inhibitor in an amount effective in treating said disease or condition and a pharmaceutically acceptable carrier.

This invention also provides a pharmaceutical composition for treating a disease or condition the treatment of which can be effected or facilitated by altering dopamine mediated neurotransmission in a mammal comprising a cdk5 inhibitor in an amount effective to inhibit cdk5 and a pharmaceutically acceptable carrier.

This invention also provides a method for treating a disease or condition the treatment of which can be effected or facilitated by altering dopamine mediated neurotransmission in a mammal comprising administering to the mammal a cdk5 inhibitor in an amount effective in inhibiting cdk5 activity.

This invention also provides a method for treating a disease or condition the treatment of which can be effected or facilitated by altering dopamine mediated neurotransmission in a mammal comprising administering to the mammal, a cdk5 inhibitor in an amount effective in treating said disease or condition.

In one embodiment of the invention, the disease or condition the treatment of which can be effected or facilitated by altering dopamine mediated neurotransmission is selected from Parkinson's disease; schizophrenia; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; personality disorder of the schizoid type; drug addiction, including narcotic (e.g. heroin, opium, and morphine), cocaine and alcohol addiction; drug withdrawal, including narcotic, cocaine and alcohol withdrawal; obsessive compulsive disorder; Tourette's syndrome; depression; a mood episode, for example a major depressive episode, a manic or mixed mood episode, a hypomanic mood episode, a depressive episode with atypical features or with melancholic features or catatonic features, or a mood episode with postpartum onset;. post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, or cyclothymic disorder; anxiety; attention deficit and hyperactivity disorder; and attention deficit disorder.

In another embodiment, the cdk5 inhibitor in the method or composition for treating a disease or condition the treatment of which can be effected or facilitated by altering dopamine mediated neurotransmission is a compound of formula 1 or a pharmaceutically-acceptable salt thereof.

This invention also provides a pharmaceutical composition for treating a disease or condition facilitated by cdk5 activity in a mammal which composition comprises a compound of formula 1 in an amount effective in inhibiting cdk5 activity and a pharmaceutically acceptable carrier.

This invention also provides a method for treating a disease or condition facilitated by cdk5 activity in a mammal which method comprises administering to the mammal a compound of formula 1 in an amount effective in inhibiting cdk5 activity.

We have also found that the compounds of formula 1 have activity in inhibiting GSK-3. The compounds of formula 1 therefore can be expected to be useful in treating diseases and conditions the treatment of which can be effected or facilitated by inhibition of GSK-3. Diseases and conditions the treatment of which can be effected or facilitated by inhibiting GSK-3 include neurodegenerative diseases and conditions. Neurodegenerative diseases and conditions are discussed above and include, but are not limited to, for example Alzheimer's disease, Parkinson's disease, Huntington's disease, amyotrophic lateral sclerosis, multiple sclerosis, stroke, cerebral ischemia, AIDS-related dementia, neurodegeneration associated with bacterial infection, multiinfarct dementia, traumatic brain injury, and spinal cord trauma. Therefore, compounds of formula 1 are effective in treating neurodegenerative diseases and conditions based on both cdk5 activity and GSK-3 activity.

Other diseases and conditions the treatment of which can be effected or facilitated by inhibiting GSK-3 include psychotic disorders and conditions, for example schizophrenia, schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type. The treatment of such diseases and conditions can also be effected or facilitated by altering dopamine mediated neurotransmission. Therefore, compounds of formula 1 are effective in treating such disorders and conditions based on both cdk5 activity and GSK-3 activity.

Other disorders and conditions the treatment of which can be effected or facilitated by inhibiting GSK-3 include mood disorders and mood episodes, for example a major depressive episode, a manic or mixed mood episode, a hypomanic mood episode, a depressive episode with atypical features or with melancholic features or catatonic features, a mood episode with postpartum onset; post-stroke depression, major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example bipolar I disorder, bipolar II disorder, and cyclothymic disorder. The treatment of such mood disorders and episodes, for example depression, can also be effected or facilitated by altering dopamine mediated neurotransmission. Therefore, compounds of formula 1 are effective in treating certain mood disorders and mood episodes based on both cdk5 activity and GSK-3 activity.

Other disorders and conditions the treatment of which can be effected or facilitated by inhibiting GSK-3 are male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; spinal cord injury; hair loss, hair thinning, and balding; immunodeficiency; and cancer.

Accordingly, the present invention also provides a pharmaceutical composition for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which composition comprises a pharmaceutically acceptable carrier and an amount of a compound of formula 1 effective in treating said disease or condition.

The present invention further provides a pharmaceutical composition for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which composition comprises a pharmaceutically acceptable carrier and an amount of a compound of formula 1 effective in inhibiting GSK-3.

The present invention also provides a method for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which method comprises administering to said mammal an amount of a compound of formula 1 effective in treating said disease or condition.

The present invention also provides a method for treating in a mammal, including a human, a disease or condition selected from male fertility and sperm motility; diabetes mellitus; impaired glucose tolerance; metabolic syndrome or syndrome X; polycystic ovary syndrome; adipogenesis and obesity; myogenesis and frailty, for example age-related decline in physical performance; acute sarcopenia, for example muscle atrophy and/or cachexia associated with burns, bed rest, limb immobilization, or major thoracic, abdominal, and/or orthopedic surgery; sepsis; hair loss, hair thinning, and balding; and immunodeficiency; which method comprises administering to said mammal an amount of a compound of formula 1 effective in inhibiting GSK-3.

The present invention further provides a method for inhibiting GSK-3 in a mammal, including a human, which method comprises administering to said mammal an amount of a compound of formula 1 effective in inhibiting GSK-3.

The present invention further provides a pharmaceutical composition for treating in a mammal a disorder selected from Alzheimer's disease, mild cognitive impairment, and age-related cognitive decline comprising a cdk5 inhibitor and a COX-II inhibitor together in an amount effective in treating said disorder, and a pharmaceutically acceptable carrier. In one embodiment, the cdk5 inhibitor is a compound of formula 1 or a pharmaceutically acceptable salt thereof.

This invention also provides a method for treating in a mammal a disorder selected from Alzheimer's disease, mild cognitive impariment, and age-related cognitive decline which method comprises administering to said mammal a cdk5 inhibitor and a COX-II inhibitor, wherein the combined amounts of the cdk5 inhibitor and the COX-II inhibitor are effective in treating said disorder. In one embodiment, the cdk5 inhibitor is a compound of formula 1 or a pharmaceutically acceptable salt thereof. The cdk5 inhibitor and the COX-II inhibitor can be administered to the mammal at the same time and/or at different times. Moreover, they may be administered together in a single pharmaceutical composition or in separate pharmaceutical compositions.

Moreover, a cdk5 inhibitor, for example a compound of formula 1 of the invention, or a pharmaceutically acceptable salt of a compound of formula 1, can be administered or formulated into a pharmaceutical composition with one or more anti-depressants or anxiolytic compounds for treatment or prevention of depression and/or anxiety.

Accordingly, this invention also provides a pharmaceutical composition for treating depression or anxiety in a mammal comprising a cdk5 inhibitor and NK-1 receptor antagonist together in an amount effective in treating depression or anxiety, and a pharmaceutically acceptable carrier. In one embodiment, the cdk5 inhibitor is a compound of formula 1 or a pharmaceutically acceptable salt thereof.

This invention further provides a method for treating depression or anxiety in a mammal which method comprises administering to said mammal a cdk5 inhibitor and an NK-1 receptor antagonist, wherein the combined amounts of the cdk5 inhibitor and the NK-1 receptor antagonist are effective in treating depression or anxiety. In one embodiment, the cdk5 inhibitor is a compound of formula 1 or a pharmaceutically acceptable salt thereof. The cdk5 inhibitor and the NK-1 receptor antagonist can be administered to the mammal at the same time and/or at different times. Moreover, they may be administered together in a single pharmaceutical composition or in separate pharmaceutical compositions.

This invention also provides a pharmaceutical composition for treating depression or anxiety in a mammal comprising a cdk5 inhibitor and a $5HT_{1D}$ receptor antagonist together in an amount effective in treating depression or anxiety, and a pharmaceutically acceptable carrier. In one embodiment, the cdk5 inhibitor is a compound of formula 1 or a pharmaceutically acceptable salt thereof.

This invention further provides a method for treating depression or anxiety in a mammal which method comprises administering to said mammal a cdk5 inhibitor and a $5HT_{1D}$ receptor antagonist, wherein the combined amounts of the cdk5 inhibitor and the $5HT_{1D}$ receptor antagonist are effective in treating depression or anxiety. In one embodiment, the cdk5 inhibitor is a compound of formula 1 or a pharmaceutically acceptable salt thereof. The cdk5 inhibitor and the $5HT_{1D}$ receptor antagonist can be administered to the mammal at the same time and/or at different times. Moreover, they may be administered together in a single pharmaceutical composition or in separate pharmaceutical compositions.

This invention also provides a pharmaceutical composition for treating depression or anxiety in a mammal comprising a cdk5 inhibitor and a SSRI together in an amount effective in treating depression or anxiety, and a pharmaceutically acceptable carrier. In one embodiment, the cdk5 inhibitor is a compound of formula 1 or a pharmaceutically acceptable salt thereof.

This invention further provides a method for treating depression or anxiety in a mammal which method comprises administering to said mammal a cdk5 inhibitor and a SSRI, wherein the combined amounts of the cdk5 inhibitor and the SSRI are effective in treating depression or anxiety. In one embodiment, the cdk5 inhibitor is a compound of formula 1 or a pharmaceutically acceptable salt thereof. The cdk5 inhibitor and the SSRI can be administered to the mammal at the same time and/or at different times. Moreover, they may be administered together in a single pharmaceutical composition or in separate pharmaceutical compositions.

This invention also provides a pharmaceutical composition for treating schizophrenia in a mammal comprising a cdk5 inhibitor and as antipsychotic selected from ziprasidone, olanzapine, risperidone, L-745870, sonepiprazole, RP 62203, NGD 941, balaperidone, flesinoxan, and gepirone, together in an amount effective in treating schizophrenia, and a pharmaceutically acceptable carrier. In one embodiment, the cdk5 inhibitor is a compound of formula 1 or a pharmaceutically acceptable salt thereof.

This invention further provides a method for treating schizophrenia in a mammal which method comprises administering to said mammal a cdk5 inhibitor and an antipsychotic selected from ziprasidone, olanzapine, risperidone, L-745870, sonepiprazole, RP 62203, NGD 941, balaperidone, flesinoxan, and gepirone, wherein the combined amounts of the cdk5 inhibitor and the antipsychotic are effective in treating schizophrenia. In one embodiment, the cdk5 inhibitor is a compound of formula 1 or a pharmaceutically acceptable salt thereof. The cdk5 inhibitor and the antipsychotic can be administered to the mammal at the same time and/or at different times. Moreover, they may be administered together in a single pharmaceutical composition or in separate pharmaceutical compositions.

This invention also provides a pharmaceutical composition for treating a disorder selected from Alzheimer's disease, mild cognitive impairment, and age-related cognitive decline in a mammal comprising a cdk5 inhibitor and an acetylcholinesterase inhibitor together in an amount effective in treating said disorder, and a pharmaceutically acceptable carrier. In one embodiment, the cdk5 inhibitor is a compound of formula 1 or a pharmaceutically acceptable salt thereof.

This invention further provides a method for treating in a mammal a disorder selected from Alzheimer's disease, mild cognitive impairment, and age-related cognitive decline, which method comprises administering to said mammal a cdk5 inhibitor and an acetylcholinesterase inhibitor, wherein the combined amounts of the cdk5 inhibitor and the acetylcholinesterase inhibitor are effective in treating said disorder. In one embodiment, the cdk5 inhibitor is a compound of formula 1 or a pharmaceutically acceptable salt thereof. The cdk5 inhibitor and the acetylcholinesterase inhibitor can be administered to the mammal at the same time and/or at different times.

This invention also provides a pharmaceutical composition for treating a disease or condition selected from stroke, spinal cord trauma, traumatic brain injury, multiinfarct dementia, epilepsy, pain, Alzheimer's disease, and senile dementia comprising a cdk5 inhibitor and TPA (tissue plasminogen activator, for example ACTIVASE) together in an amount effective in treating said disorder, and a pharmaceutically acceptable carrier. In one embodiment, the cdk5 inhibitor is a compound of formula 1 or a pharmaceutically acceptable salt thereof.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a cdk5 inhibitor and TPA, wherein the combined amounts of the cdk5 inhibitor and the TPA are effective in treating said disease or condition. In one embodiment, the cdk5 inhibitor is a compound of formula 1 or a pharmaceutically acceptable salt thereof. The cdk5 inhibitor and the TPA can be administered to the mammal at the same time and/or at different times. Moreover, they may be administered together in a single pharmaceutical composition or in separate pharmaceutical compositions.

This invention also provides a pharmaceutical composition for treating a disease or condition selected from stroke, spinal cord trauma, traumatic brain injury, multiinfarct dementia, epilepsy, pain, Alzheimer's disease, and senile dementia in a mammal comprising a cdk5 inhibitor and NIF (neutrophil inhibitory factor) together in an amount effective in treating said disorder, and a pharmaceutically acceptable carrier. In one embodiment, the cdk5 inhibitor is a compound of formula 1 or a pharmaceutically acceptable salt thereof.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a cdk5 inhibitor and NIF, wherein the combined amounts of the cdk5 inhibitor and the NIF are effective in treating said disease or condition. In one embodiment, the cdk5 inhibitor is a compound of formula 1 or a pharmaceutically acceptable salt thereof. The cdk5 inhibitor and the NIF can be administered to the mammal at the same time and/or at different times. Moreover, they may be administered together in a single pharmaceutical composition or in separate pharmaceutical compositions.

This invention also provides a pharmaceutical composition for treating a disease or condition selected from Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinece, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis in a mammal comprising a cdk5 inhibitor and an NMDA receptor antagonist together in an amount effective in treating said disorder, and a pharmaceutically acceptable carrier. In one embodiment, the cdk5 inhibitor is a compound of formula 1 or a pharmaceutically acceptable salt thereof.

This invention further provides a method for treating in a mammal a disease or condition selected from Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinece, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, and subacute sclerosing panencephalistis, which method comprises administering to said mammal a cdk5 inhibitor and an NMDA receptor antagonist, wherein the combined amounts of the cdk5 inhibitor and the NMDA receptor antagonist are effective in treating said disease or condition. In one embodiment, the cdk5 inhibitor is a compound of formula 1 or a pharmaceutically acceptable salt thereof. The cdk5 inhibitor and the NMDA receptor antagonist can be administered to the mammal at the same time and/or at different times. Moreover, they may be administered together in a single pharmaceutical composition or in separate pharmaceutical compositions.

This invention also provides a pharmaceutical composition for treating a disease or condition selected from stroke, spinal cord trauma, traumatic brain injury, multiinfarct dementia, epilepsy, pain, Alzheimer's disease, and senile dementia in a mammal comprising a cdk5 inhibitor and a potassium channel modulator together in an amount effective in treating said disorder, and a pharmaceutically acceptable carrier. In one embodiment, the cdk5 inhibitor is a compound of formula 1 or a pharmaceutically acceptable salt thereof.

This invention further provides a method for treating in a mammal a disease or condition selected from stroke, spinal cord trauma, traumatic brain injury, multiinfarct dementia, epilepsy, pain, Alzheimer's disease, and senile dementia, which method comprises administering to said mammal a cdk5 inhibitor and a potassium channel modulator, wherein the combined amounts of the cdk5 inhibitor and the potassium channel modulator are effective in treating said disease or condition. In one embodiment, the cdk5 inhibitor is a compound of formula 1 or a pharmaceutically acceptable salt thereof. The cdk5 inhibitor and the potassium channel modulator can be administered to the mammal at the same time and/or at different times. Moreover, they may be administered together in a single pharmaceutical composition or in separate pharmaceutical compositions.

The terms "treatment", "treating", and the like, refers to reversing, alleviating, or inhibiting the progress of the disease or condition to which such term applies, or one or more symptoms of such disease or condition. As used herein, these terms also encompass, depending on the condition of the patient, preventing the onset of a disese or condition, or of symptoms associated with a disease or condition, including reducing the severity of a disease or condition or symptoms associated therewith prior to affliction with said disease or condition. Such prevention or reduction prior to affliction refers to administration of the compound of the invention to a subject that is not at the time of administration afflicted with the disease or condition. "Preventing" also encompasses preventing the recurrence of a disease or condition or of symptoms associated therewith.

"Mammal", as used herein, and unless otherwise indicated, means any mammal. The term "mammal" includes, for example and without limitation, dogs, cats, and humans.

"Abnormal cell growth", as used herein, refers to cell growth, either malignant (e.g. as in cancer) or benign, that is independent of normal regulatory mechanisms (e.g., loss of contact inhibition). Examples of benign proliferative diseases are psoriasis, benign prostatic hypertrophy, human papilloma virus (HPV), and restinosis.

"Neurodegenerative diseases and conditions", as used herein, refers to diseases and conditions having associated therewith degeneration of neurons. Conditions and diseases that are neurodegenerative in nature are generally known to those of ordinary skill in the art.

References herein to diseases and conditions "the treatment of which can be effected or facilitated by altering dopamine mediated neurotransmission" mean a disease or condition that is caused at least in part by dopamine neurotransmission, or a disease or condition that result in abnormal dopamine neurotransmission, thus contributing to symptoms or manifestations of the disease or condition.

References herein to diseases and conditions "the treatment of which can be effected or faciliatated by decreasing cdk5 activity" mean a disease or condition that is caused at least in part by cdk5 activity, or a disease or condition that results in abnormal cdk5 activity that contributes to symptoms or manifestations of the disease or condition.

An "amount effective to inhibit cdk5 activity" as used herein refers to an amount of a compound sufficient to bind to the enzyme cdk5 with the effect of decreasing cdk5 activity.

An "amount effective to inhibit cdk2 activity" as used herein refers to an amount of a compound sufficient to bind to the enzyme cdk2 with the effect of decreasing cdk2 activity.

DETAILED DESCRIPTION OF THE INVENTION

Compounds of the formula 1, above, and their pharmaceutically acceptable salts, can be prepared according to the following reaction Schemes and discussion. Unless otherwise indicated $R^1$, $R^2$, $R^3$, and $R^4$ are as defined above. Isolation and purification of the products is accomplished by standard procedures which are known to a chemist of ordinary skill.

As used herein, the expression "reaction inert solvent" refers to a solvent system in which the components do not interact with starting materials, reagents, or intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991.

Scheme 1 illustrates methods suitable for preparing compounds of formula 1 wherein $R^3$ is —C(═O)NH—, —C(═O)O—, or —C(═O)(CR$^{10}$R$^{11}$)$_n$—. Referring to Scheme 1, treatment of a solution of 1,4-dinitroimidazole (*J. Phys. Chem.* (1995) Vol. 99, pp. 5009–1015) in dimethylsulfoxide (DMSO), pyridine-water, water, acetonitrile-water, an alcohol, or an alcohol-water solvent system, but preferably in a lower alcohol such as methanol, from about −20° C. to about 50° C., preferably from about −5° C. to 35° C., with a primary alkyl or aryl amine affords 1-N-substituted-4-nitroimidazoles of formula 2. 1,4-Dinitroimidazole is a highly energetic, semi-stable substance and should be stored in a freezer at all times it is not in use. Thermodynamic measurements have shown that it can potentially generate enough energy at 35° C. under adiabatic conditions to violently explode. Extreme caution should be exercised at all times using this material. Reduction of the nitro compound of formula 2 to the amine of formula 3 may be accomplished by exposing a mixture of a compound of formula 2 and a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. Palladium is the preferred noble metal catalyst. The metal may be conveniently suspended on an inert solid support such as charcoal. After the compound of formula 2 has been consumed, the mixture is filtered and the resulting amine of formula 3 is reacted immediately with an acid chloride ClC(═O)(CR$^{10}$R$^{11}$)$_n$R$^4$, acid anhydride (R$^4$(CR$^{10}$R$^{11}$)$_n$C(═O))$_2$O, or an activated carboxylic acid derivative XC(═O)(CR$^{10}$R$^{11}$)$_n$R$^4$, in the presence of a base, such as triethylamine, diisopropylethylamine, pyridine, or 2,6-lutidine, from about −78° C. to 40° C. 1-Propanephosphonic acid cyclic anhydride and triethylamine are a preferred combination. The activated carboxylic acid derivative is prepared from the carboxylic acid HOC(═O)(CR$^{10}$R$^{11}$)$_n$R$^4$ and a known activating reagent such as dicyclohexyl carbodiimide, 1-(3-dimethylaminopropyl)-3-ethylcarbodiimide hydrochloride, carbonyl diimidazole, 1-propanephosphonic acid cyclic anhyrdide, alkyl or aryl chloroformate, bis(2-oxo-3-oxazolidinyl)phosphinic chloride, benzotriazol-1-yloxy-tris(dimethylamino)phosphonium hexafluorophosphate, or any other such standard literature reagents. This procedure affords a compound of formula 1B where $R^3$ is —C(═O)(CR$^{10}$R$^{11}$)$_n$—.

Alternatively, following filtration, the amine of formula 3 can be treated with a base, such as triethylamine, diisopropylethylamine, pyridine, or 2,6-lutidine, and an alkyl- or aryl-chloroformate, from about −78° C. to 40° C., where −78° C. to −40° C. are preferred, to afford a compound of formula 1A where $R^3$ is —C(═O)O— and $R^4$ is phenyl. Diisopropylethylamine and phenyl chloroformate are a preferred combination. Subsequent treatment of phenyl carbamate of formula 1A with a primary or secondary amine in a solvent such as dioxane, dimethylformamide, or acetonitrile, at a temperature between about 40° C. and 90° C., affords the corresponding urea product 1C where $R^3$ is —C(═O)NR$^9$— and $R^4$ is phenyl or heteroaryl. A 1:1 mixture of dioxane-dimethylformamide and 70° C. are preferred.

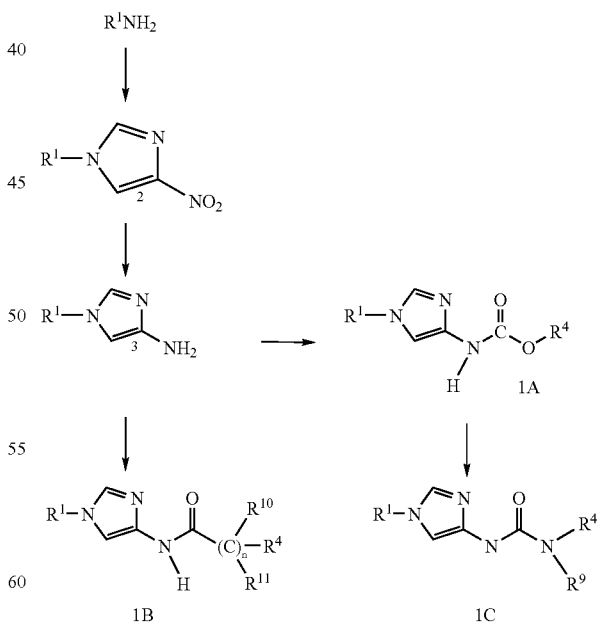

Scheme 1

A method of preparing compounds of formula 1, wherein $R^1$ is substituted with $R^5$ and $R^5$ is NHC(═O)R$^8$, is shown in Scheme 2. Treating the compound of formula 4 where $R^5$═OH, with an alkyl- or aryl-sulfonyl chloride, where p-toluenesulfonyl chloride (TosCl) is preferred, in a reaction inert solvent such as tetrahydrofuran, methylene chloride or chloroform, where methylene chloride is preferred, at a temperature from about −10° C. to about 30° C., in the presence of an amine base such as triethylamine, diisopropylethylamine, pyridine, or 2,6-lutidine, where triethylamine is preferred, and catalytic 4-N,N-dimethylaminopyridine, affords a compound of formula 5 wherein $R^5$ is $CH_3(C_6H_4)SO_3$ (TosO). Treatment of the tosylate thus formed with an alkali metal salt of azide, wherein sodium azide is preferred, in a polar solvent such as dimethylformamide, dimethylsulfoxide, a lower alcohol, water, or a mixture of these solvents, wherein an ethanol-water mixture is preferred, at a temperature from about 20° C. to 130° C., where 90° C. to 110° C. are preferred, produces a compound of formula 6, wherein $R^5$ is $N_3$.

Treatment of the azide under selective reducing conditions, such as trialkyl- or triarylphosphine and water, wherein triphenylphosphine is preferred, in a solvent such as tetrahydrofuran, dioxane, acetonitrile, or a mixture thereof, where tetrahydrofuran is preferred, affords a compound of formula 7 where $R^5$ is $NH_2$. The primary amino group of the compound of formula 7 thus formed ($R^5=NH_2$) can be derivatized via reaction with a chloroformate, isocyanate, carbamoylyl chloride, acid chloride, acid anhydride, or an activated carboxylic acid derivative. The activated carboxylic acid derivative is prepared from the carboxylic acid and a known activating reagent such as dicyclohexyl carbodiimide, 1-(3-dimethylaminopropyl)-3-ethylcarbodiimide, carbonyl diimidazole, 1-propanephosphonic acid cyclic anhyrdide, alkyl chloroformate, bis(2-oxo-3-oxazolidinyl) phosphinic chloride, benzotriazol-1-yloxy-tris(dimethylamino)phosphonium hexafluorophosphate, or any other such standard literature reagents in the presence of an amine base if necessary, such as triethylamine, diisopropylethylamine, pyridine, or 2,6-lutidine, wherein 1-(3-dimethylaminopropyl)-3-ethylcarbodiimide hydrochloride is preferred, from about −78° C. to 80° C., where 0° C. to 40° C. is preferred. Tetrahydrofuran and methylene chloride are preferred solvents.

Conversion of a compound of the formula 8 thus formed wherein $R^5$ is —NHC(=O)$R^8$ to a compound of formula 1D ($R^5$ is NHC(=O)$R^8$; $R^3$ is C(=O)(CR$^{10}$R$^{11}$)$_n$R$^4$) may be accomplished by exposing a mixture of the compound of formula 8 and a noble metal catalyst, wherein palladium is a preferred noble metal catalyst, wherein the metal may be conveniently suspended on an inert solid support such as charcoal, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. After the compound of formula 8 has been consumed, the mixture is filtered and the resulting amine is acylated immediately by reaction with acid chloride, acid anhydride, or an activated carboxylic acid derivative, in the presence of an amine base if appropriate, such as triethylamine, diisopropylethylamine, pyridine, or 2,6-lutidine, wherein 1-propanephosphonic acid cyclic anhyrdide and triethylamine are a preferred combination, from about −78° C. to 40° C., to afford the N-acylated product of formula 1D. The activated carboxylic acid derivative is prepared from the carboxylic acid and a known activating reagent such as dicyclohexyl carbodiimide, 1-(3-dimethylaminopropyl)-3-ethylcarbodiimide, carbonyl diimidazole, 1-propanephosphonic acid cyclic anhyrdide, alkyl chloroformate, bis(2-oxo-3-oxazolidinyl)phosphinic chloride, benzotriazol-1-yloxy-tris(dimethylamino)phosphonium hexafluorophosphate, or any other such standard literature reagent.

If an aryl chloroformate or heteroaryl chloroformate is used in the above acylation instead of an acid chloride, acid anhydride, or an activated carboxylic acid derivative, an aryl carbamate 1E results. the resulting aryl carbamate 1E ($R^3$ is C(=O)O— and $R^4$ is aryl or heteroaryl) can be treated with an amine in a solvent such as dioxane, dimethylformamide, or acetonitrile, where a 1:1 mixture of dioxane-dimethylformamide is preferred, at a temperature between about 40° C. and 90° C., where 70° C. is preferred, to afford the corresponding urea product of formula 1F ($R^3$ is —C(=O)NR$^9$—, $R^4$ is aryl or heteroaryl).

Scheme 2

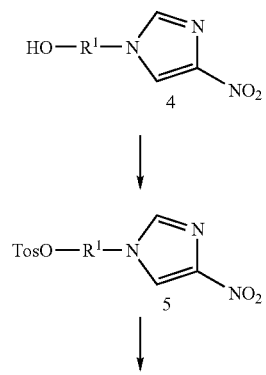

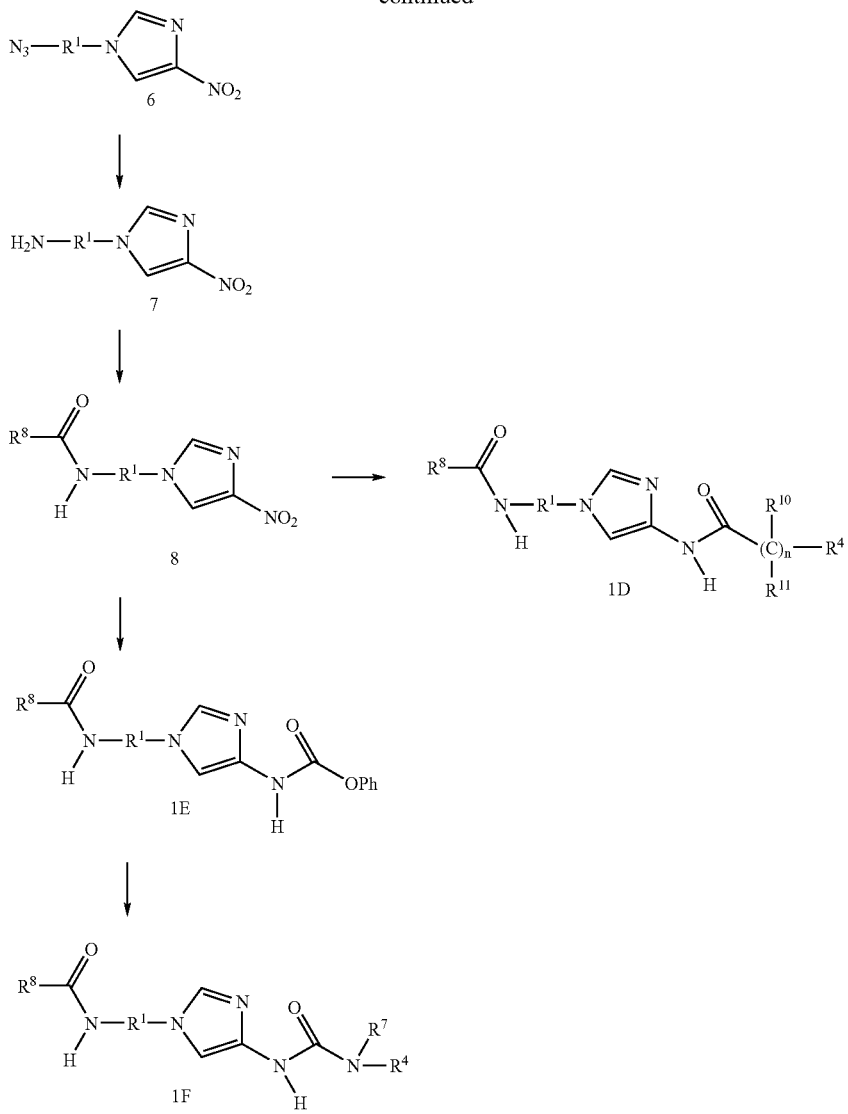

-continued

An alternative method of preparing compounds of formula 1, wherein, $R^5$ is —NHC(=O)$R^8$, is shown in Scheme 3. Treating compound 4 where $R^5$ is OH, with an alkyl- or aryl-sulfonyl chloride, p-toluenesulfonyl chloride (TosCl) being preferred, in a reaction inert solvent such as tetrahydrofuran, methylene chloride or chloroform, where methylene chloride is preferred, at a temperature from about −10° C. to about 30° C., in the presence of an amine base such as triethylamine, diisopropylethylamine, pyridine, or 2,6-lutidine, and 4-N,N-dimethylaminopyridine, affords a compound of formula 5 wherein $R^5$ is $CH_3(C_6H_4)SO_3$ (TosO). Triethylamine is the preferred amine base. Conversion of a compound of formula 5 ($R^5$ is TosO) to a compound of formula 1G ($R^5$ is TosO, $R^3$ is C(=O)($CR^{10}R^{11})_n R^4$) may be accomplished by exposing a mixture of the compound of formula 5 ($R^5$ is TosO) and a noble metal catalyst, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. Palladium is a preferred noble metal catalyst. The metal may be conveniently suspended on an inert solid support such as charcoal. After the compound 5 has been consumed, the mixture is filtered and the resulting amine is reacted immediately with acid chloride, acid anhydride, or an activated carboxylic acid derivative, in the presence of an amine base if appropriate, such as triethylamine, diisopropylethylamine, pyridine, or 2,6-lutidine, wherein 1-propanephosphonic acid cyclic anhyrdide and triethylamine are a preferred combination, from about −78° C. to 40° C., to afford the N-acylated product of formula 1G. The activated carboxylic acid derivative is prepared from the carboxylic acid and a known activating reagent such as dicyclohexyl carbodiimide, 1-(3-dimethylaminopropyl)-3-ethylcarbodiimide, carbonyl diimidazole, 1-propanephosphonic acid cyclic anhyrdide, alkyl chloroformate, bis(2-oxo-3-oxazolidinyl)phosphinic chloride, benzotriazol-1-yloxy-tris(dimethylamino)phosphonium hexafluorophosphate, or any other such standard literature reagents.

Treatment of the compound of formula 1G ($R^5$ is TosO, $R^3$ is —C(=O)($CR^{10}R^{11})_n$— with an alkali metal salt of azide, wherein sodium azide is preferred, in a polar solvent such as dimethylformamide, dimethylsulfoxide, a lower alcohol, water, or a mixture of these solvents, wherein an ethanol-water mixture is preferred, at a temperature from about 20° C. to 130° C., where 90° C. to 110° C. are preferred, can be used to produce a compound of formula 1H, wherein $R^5$ is $N_3$. Subsequent reduction of azide of formula 1H ($R^5$ is $N_3$) may be accomplished by exposing a mixture of the compound of formula 1H ($R^5$ is $N_3$) and a noble metal catalyst, wherein palladium is a preferred noble metal catalyst, wherein the metal may be conveniently suspended on an inert solid support such as charcoal, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres.

Alternatively, reduction of the azide of formula 1H ($R^5$ is $N_3$) can be by treatment with a trialky- or triarylphosphine and water, wherein triphenylphosphine is preferred, in a solvent such as tetrahydrofuran, dioxane, or acetonitrile, where tetrahydrofuran is preferred. The primary amino group of the compound of formula 1I ($R^5$ is $NH_2$) can be derivatized via reaction with a chloroformate, isocyanate, carbamoylyl chloride, acid chloride, acid anhydride, or an activated carboxylic acid derivative, wherein the activated carboxylic acid derivative is prepared from the carboxylic acid and a known activating reagent such as dicyclohexyl carbodiimide, 1-(3-dimethylaminopropyl)-3-ethylcarbodiimide, carbonyl diimidazole, 1-propanephosphonic acid cyclic anhyrdide, alkyl chloroformate, bis(2-oxo-3-oxazolidinyl)phosphinic chloride, benzotriazol-1-yloxy-tris(dimethylamino)phosphonium hexafluorophosphate, or any other such standard literature reagents is in the presence of an amine base if necessary, such as triethylamine, diisopropylethylamine, pyridine, or 2,6-lutidine, wherein 1-(3-dimethylaminopropyl)-3-ethylcarbodiimide hydrochloride is preferred, from about −78° C. to 80° C., where 0° C. to 40° C. is preferred. Tetrahydrofuran and methylene chloride are preferred solvents.

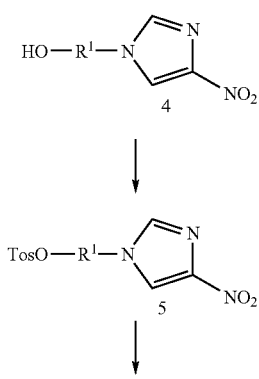

Scheme 3

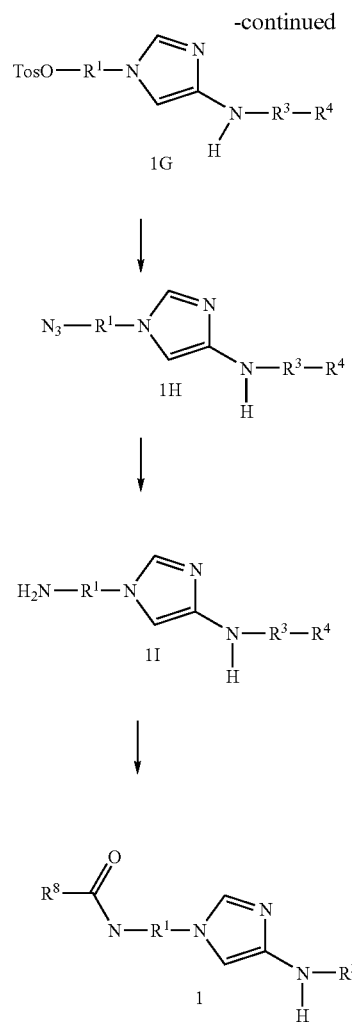

Compounds of formula 1, wherein $R^3$ is $-(CR^{10}R^{11})_n-$ may be prepared according to Scheme 4. Referring to Scheme 4, treatment of a solution of 4-bromoimidazole with a base, such as sodium hydride, potassium hydride, lithium hydride, cesium carbonate, sodium hydroxide, potassium hydroxide, cesium hydroxide, lithium diisopropyl amide, sodium amide, potassium hexamethyldisilazide, sodium hexamethyldisilazide, sodium tert-butoxide, or potassium tert-butoxide, in a reaction inert solvent such as tetrahydrofuran, 1,4-dioxane, N,N-dimethylformamide, dimethylsulfoxide, or toluene, from about −20° C. to 150° C., where 20° C. to 100° C. is preferred, in the absence or presence of a phase transfer catalyst, such as tetra-n-butylammonium chloride, tetra-n-butylammonium bromide, tetra-n-butylammonium iodide, benzyltrimethyl ammonium chloride, benzyltrimethyl ammonium bromide, or benzyltrimethyl ammonium fluoride, followed by the addition of an alkyl, allylic, or benzylic chloride, bromide, iodide, alkyl sulfonate, aryl sulfonate, or triflate, affords a mixture of 1-substituted-4-bromoimidazole (9) and 1-substituted-5-bromoimidazole (10), which can be separated using methods known to one skilled in the art.

Alternatively, treatment of 4-bromoimidazole with an allylic fluoride, chloride, bromide, iodide, acetate, or carbonate, where the allylic carbonate is preferred, in a reaction inert solvent, such as tetrahydrofuran, 1,2-dichloroethane, 1,4-dioxane, dimethylsulfoxide, or N,N-dimethylformamide, where tetrahydrofuran is preferred, in the presence of a palladium catalyst, such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride, where palladium tetrakis(triphenylphosine) or palladium (II) acetate are preferred, in the presence or absence of a phosphine ligand, such as triphenylphosine, tri-o-tolylphosphine, tri-tert-butylphosphine, 1,2-bis(diphenylphosphino)ethane, or 1,3-bis(diphenylphosphino)propane, from about 0° C. to 100° C., where 50° C. to 80° C. is preferred, provides a mixture of 1-substituted-4-bromoimidazole (9) and 1-substituted-5-bromoimidazole (10).

Treatment of 1-substituted-4-bromoimidazole (9) with an intermediate of the formula —NH$_2$(CR$^{10}$R$^{11}$)$_n$R$^4$ and a palladium catalyst such as palladium (II) acetate, allyl palladium chloride dimer, tris(dibenzylideneacetone)dipalladium (0), tris(dibenzylideneacetone)dipalladium (0) chloroform adduct, or palladium (II) chloride, where palladium (II) acetate, tris(dibenzylideneacetone)dipalladium (0), and tris(dibenzylideneacetone)dipalladium (0) chloroform adduct are preferred, and a phosphine ligand, such as BINAP, 2-biphenyl dicyclohexylphosphine, 2-biphenyl di-tert-butylphosphine, or 2-N,N-dimethylamino-2'-diphenylphosphino biphenyl, where 2-N,N-dimethylamino-2'-diphenylphosphino biphenyl is preferred, and a base, such as sodium tert-butoxide, cesium carbonate, or potassium phosphate (K$_3$PO$_4$), where potassium phosphate is preferred, in a reaction inert solvent, such as toluene, 1,4-dioxane, or tetrahydrofuran, from about 0° C. to 150° C. where 20° C. to 110° C. is preferred, affords the coupled product 1.

Scheme 4

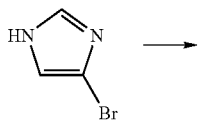

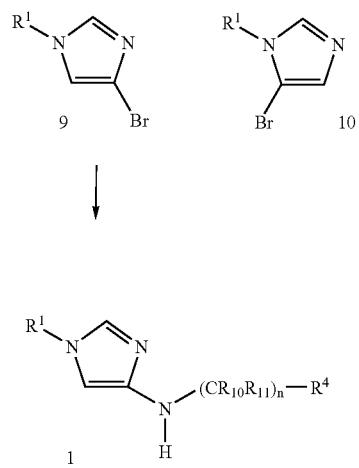

An alternative method for synthesizing compounds of formula 1, wherein R$^3$ is —C(=O)(CR$^{10}$R$^{11}$)$_n$— is illustrated in Scheme 5, below. Treatment of ethyl-2-isocyano-3-N,N-dimethylamino acrylate (11) with a primary amine, R$^1$—NH$_2$, in a solvent such as n-butanol, n-propanol, I-propanol, or ethanol, or in the absence of solvent, where either n-propanol or no solvent are preferred, from about 23° C. to about 200° C., where from about 60° C. to about 150° C. is preferred, affords imidazoles of formula 12. Treatment of N,O-dimethyl hydroxyl amine hydrochloride with trimethylaluminum in 1,2-dichloroethane followed by the addition of 12 and heating at about 30° C. to about 80° C., where a temperature of about 50° C. is preferred, affords imidazole 13. Addition of an organometallic reagent M-(CR$^{10}$R$^{11}$)$_n$R$^4$, where M may be either lithium or magnesium halide, where magnesium halide is preferred, to a solution of 13 in a solvent such as tetrahydrofuran, methylene chloride, or diethyl ether, from a temperature about −50° C. to about 30° C., where a range of about −20° C. to about 0° C. is preferred, affords 14. Addition of 14 to a mixture of hydroxyl amine hydrochloride and potassium acetate in a lower alcohol solvent, where ethanol is preferred, at about 23° C., yields oxime 15 as a mixture of isomers. Treatment of an acetone solution of oxime 15 at about 0° C. with aqueous sodium hydroxide followed by paratoluenesulfonyl chloride yields a mixture of O-sulfonyl compounds following extractive workup. Dissolution of the crude material in a non-polar solvent such as benzene, hexanes, or toluene, where benzene is preferred, and application to a column of alumina followed by elution with chloroform-methanol (about 10:1) after approximately five minutes provides a compound 1B and a regioisomer from the Beckmann rearrangement.

Scheme 5

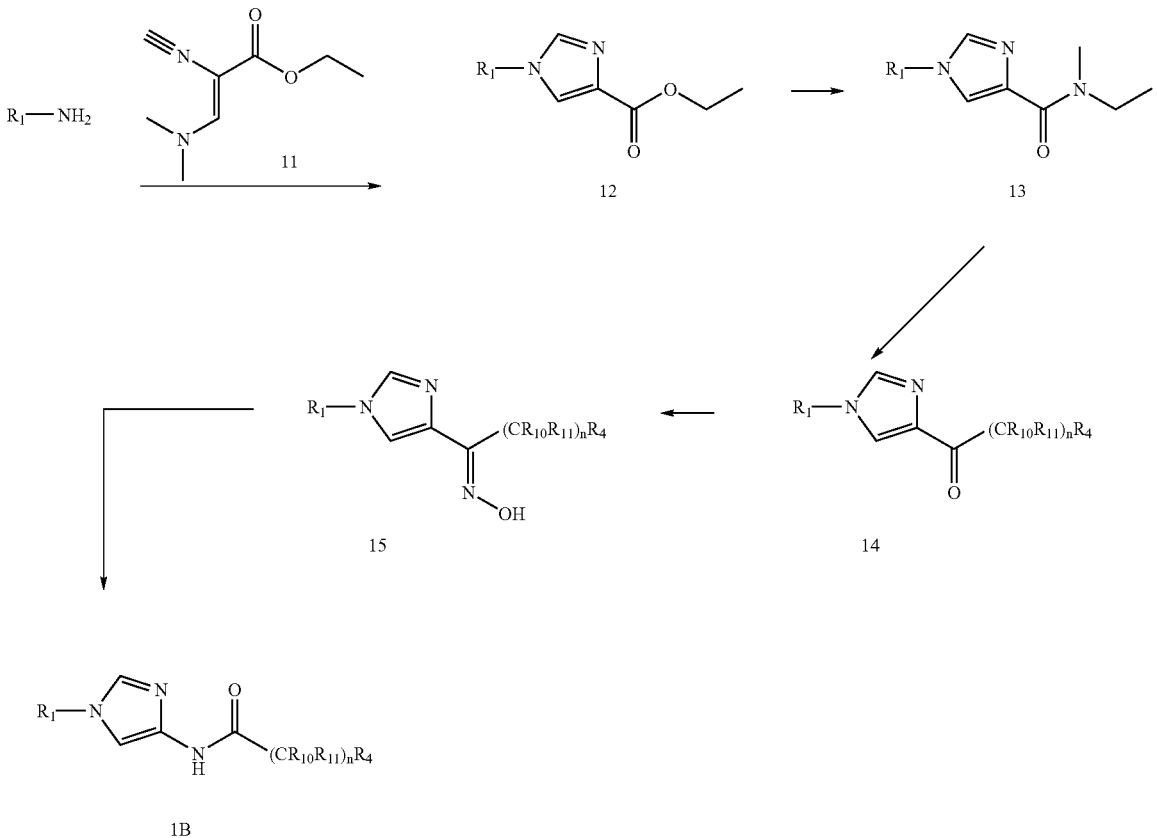

Compounds of formula 1J may also be prepared by the method illustrated in Scheme 6 below. A key starting material for this synthesis is the double-bond containing compound (a compound of formula X) substituted with the group $ER^5$ and one to three groups selected from $R^5$ (X), where $ER^5$ is defined as an electron-withdrawing group chosen from $C(=O)R^7$, $C(=O)OR^7$, $C(=O)NR^7R^8$, $S(=O)_2R^7$, $S(=O)_2NR^7R^8$, $S(=O)_2OR^7$, cyano, and heteroaryl. Additionally, compounds of formula X may be wherein $ER^5$ is connected to one of the groups $R^5$ or directly to the carbon-carbon double bond to form a ring and thus includes compounds such as 2-cyclopentene-1-one and 2-cyclohexene-1-one. Alternatively, compounds of formula X where L is defined as Cl, Br, I, $OC(=O)R^7$, or $OS(=O)_2R^7$ may be used as starting materials; examples of such compounds are 3-chloro-1-cyclopentanone, 3-acetoxy-1-cyclobutanone. Thus, referring to Scheme 6, treatment of a salt of 4 (5)-nitroimidazole, where the salt is sodium, potassium, cesium, 1,8-diazabicyclo [5.4.0]undec-7-ene (DBU) or tetraalkyl ammonium, where tetra n-butylammonium and DBU are the preferred salts, with intermediates 16 or 17 in a solvent such as acetonitrile, methylene chloride, 1,2-dichloroethane, or chloroform, where acetonitrile is the preferred solvent, at a temperature from about –60° C. to about 50° C., where –20° C. to 23° C. is the preferred range, affords addition products of formula 2A. Reduction of nitro compound 2A may be accomplished by exposing a mixture of 2A and a noble metal catalyst, wherein palladium is a preferred noble metal catalyst, wherein the metal may be conveniently suspended on an inert solid support such as charcoal, in a solvent such as ethyl acetate, tetrahydrofuran, dioxane, or a mixture thereof, to an atmosphere of hydrogen gas at a pressure of about 1 to 100 atmospheres, where a preferred pressure of hydrogen gas is about one to about ten atmospheres. After 2A has been consumed, the mixture is filtered and the resulting amine is reacted immediately with an acid chloride $ClC(=O)(CR^{10}R^{11})_nR^4$, acid anhydride $(R^4(CR^{10}R^{11})_nC(=O))_2O$, or an activated carboxylic acid derivative $XC(=O)(CR^{10}R^{11})_nR^4$, in the presence of a base, such as triethylamine, diisopropylethylamine, pyridine, or 2,6-lutidine, wherein , 1-propanephosphonic acid cyclic anhyrdide and triethylamine are a preferred combination, from about –78° C. to about 40° C., to afford 1J. The activated carboxylic acid derivative is prepared from the carboxylic acid $HOC(=O)(CR^{10}R^{11})_nR^4$ and known activating reagents such as dicyclohexyl carbodiimide, 1-(3-dimethylaminopropyl)-3-ethylcarbodiimide hydrochloride, carbonyl diimidazole, 1-propanephosphonic acid cyclic anhyrdide, alkyl or aryl chloroformate, bis(2-oxo-3-oxazolidinyl)phosphinic chloride, benzotriazol-1-yloxy-tris(dimethylamino)phosphonium hexafluorophosphate, or any other such standard literature reagents.

Alternatively, following filtration, the intermediate amine can be treated with a base, such as triethylamine, diisopropylethylamine, pyridine, or 2,6-lutidine, and an alkyl- or aryl-chloroformate, where diisopropylethylamine and phenyl chloroformate are a preferred combination, from about −78° C. to about 40° C., where about −78° C. to about −40° C. are preferred, to afford 1K.

Subsequent treatment of 1K with a primary or secondary amine in a solvent such as dioxane, dimethylformamide, or acetonitrile, where a 1:1 mixture of dioxane-dimethylformamide is preferred, at a temperature between about 40° C. and about 90° C., where about 70° C. is preferred, affords the corresponding urea product 1L.

Subsequent transformations of compounds 2A, 1J, 1K, and 1L using methods known to one skilled in the art may be carried out to provide further compounds of formula 1 that are described in this application.

Compounds of formula 1 as described herein, wherein $R^2$ is other than hydrogen can be prepared by transformations of the compounds of formula 1 described herein wherein $R^2$ is hydrogen using methods that are well known in the art. For example, compounds of formula 1 wherein $R^2$ is F can be prepared by treating compounds of formula 1 wherein $R^2$ is hydrogen, for example compounds of formula 1A, 1B, and 1C referred to in Scheme 1, supra, with N-fluorobenzenesulfonimide in toluene, xylenes, or dioxane, from about room temperature to about 150° C., preferably from about 100° C. to about 120° C.

carriers include inert solid diluents or fillers, sterile aqueous solutions and various organic solvents. The pharmaceutical compositions formed by combining a compound of formula 1 or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweeten-

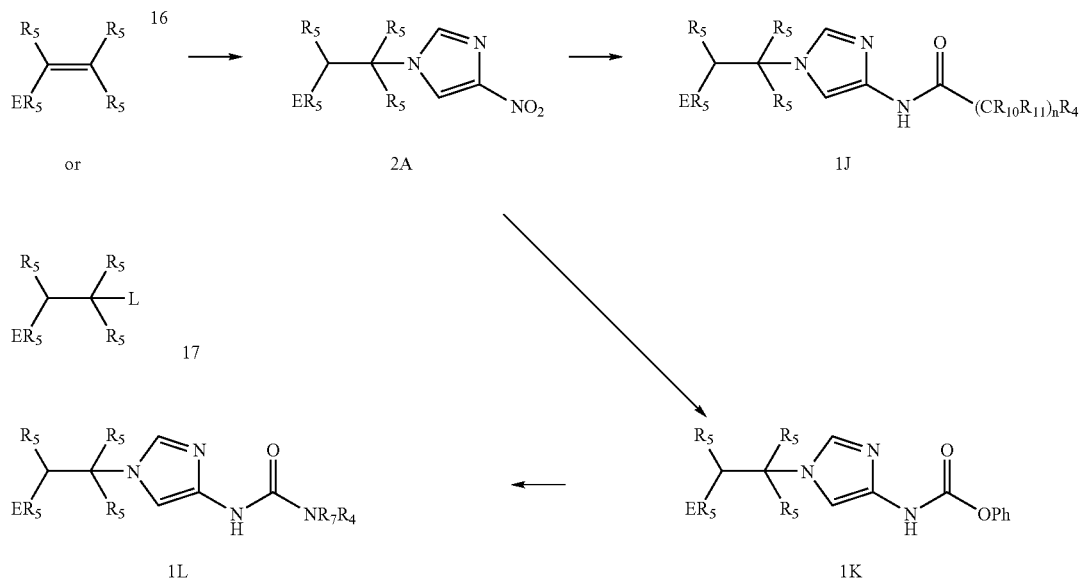

Pharmaceutically acceptable salts of a compound of formula 1 can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical ing or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula 1 or a pharmaceutically acceptable salt thereof can be administered orally, transdermally (e.g., through the use of a patch), parenterally (e.g. intravenously), rectally, or topically. In general, the daily dosage for treating a neurodegenerative disease or condition or the disease or condition the treatment of which can be effected or facilitated by altering dopamine mediated neurotransmission will generally range from about 0.0001 to about 10.0 mg/kg body weight of the patient to be treated. The daily dosage for treating cancer or disease or condition involving abnormal cell growth of a benign nature will also generally range from about 0.0001 to about 500 mg/kg body weight of the patient to be treated. As an example, a compound of the formula 1 or a pharmaceutically acceptable salt thereof can be administered for treatment of a neurodegenerative disorder to an adult human of average weight (about 70 kg) in a dose ranging from about 0.01 mg up to about 1000 mg per day, preferably from about 0.1 to about 500 mg per day, in single or divided (i.e., multiple) portions. The daily dosage for treating diabetes, sperm motility, hair loss, or any other disease or condition that can be treated by inhibiting GSK-3 will generally range from about 0.0001 to about 10.0 mg/kg body weight of the patient to be treated. Variations based on the aforementioned dosage ranges may be made by a physician of ordinary skill taking into account known considerations such as the weight, age, and condition of the person being treated, the severity of the affliction, and the particular route of administration chosen.

The compounds of formula 1 and their pharmaceutically acceptable salts can furthermore also be administered or formulated into a pharmaceutical composition with an amount of one or more substances selected from anti-angiogenesis agents, signal transduction inhibitors, and anti-proliferative agents, which amounts are together effective in inhibiting abnormal cell growth.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of formula 1 in the methods and pharmaceutical compositions described herein for treatment of abnormal cell growth, including cancer. Examples of useful COX-II inhibitors include CELEBREX™ (celecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino ]-tetrahydro-pyran-3-carboxylic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

The effective amount of a COX-II inhibitor in combination with a cdk5 inhibitor, for example a compound of formula 1, can generally be determined by a person of ordinary skill. A proposed daily effective dose range for a COX-II inhibitor in combination with a cdk5 inhibitor is from about 0.1 to about 25 mg/kg body weight. The effective daily amount of the cdk5 inhibitor generally will be between about 0.0001 to about 10 mg/kg body weight. In some instances the amount of COX-II inhibitor and/or cdk5 inhibitor in the combination may be less than would be required on an individual basis to achieve the same desired effect in inhibiting abnormal cell growth.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA). Such combinations are useful for treating and preventing abnormal cell growth, including cancer, as described herein.

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8,1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can also be combined with a compound of formula 1, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with a compound of formula 1, in accordance with the present invention.

A compound of formula 1, can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as farnesyl protein transferase inhibitors. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The compounds of formula 1 can also be administered in a method for inhibiting abnormal cell growth in a mammal in combination with radiation therapy. Techniques for administering radiation therapy are known in the art, and these techniques can be used in the combination therapy described herein. The administration of the compound of the invention in this combination therapy can be determined as described herein.

Cdk5 inhibitors, such as compounds of formula 1, can also be administered in combination with a COX-II inhibitor for treating Alzheimer's disease, mild cognitive impairment, or age-related cognitive decline. Specific examples of COX-II inhibitors useful in this aspect of the invention are provided above, wherein use of a COX-II inhibitor in combination with a compound of formula 1 for treatment of abnormal cell growth is described. The effective amount of a COX-II inhibitor in combination with a cdk5 inhibitor, for example a compound of formula 1, can generally be determined by a person of ordinary skill. A proposed effective daily dose range for a COX-II inhibitor in combination with a cdk5 inhibitor is from about 0.1 to about 25 mg/kg body weight. The daily effective amount of the cdk5 inhibitor generally will be between about 0.0001 to about 10 mg/kg body weight. In some instances the amount of COX-II inhibitor and/or the amount of cdk5 inhibitor in the combination may be less than would be required on an individual basis to achieve the same desired effect in treating Alzheimer's disease, mild cognitive impairment, or age-related cognitive decline.

Cdk5 inhibitors, such as compounds of formula 1, can also be administered in combination with an NK-1 receptor antagonist for treatment of depression or anxiety. An NK-1 receptor antagonist, as recited herein, is a substance that is able to antagonize NK-1 receptors, thereby inhibiting tachykinin-mediated responses, such as responses mediated by substance P. Various NK-1 receptor antagonists are known in the art, and any such NK-1 receptor antagonist can be utilized in the present invention as described above in combination with a cdk5 inhibitor, for example a compound of formula 1. NK-1 receptor antagonists are described in, for example, U.S. Pat. No. 5,716,965 (issued Feb. 10, 1998); U.S. Pat. No. 5,852,038 (issued Dec. 22, 1998); WO 90/05729 (International Publication Date May 31, 1990); U.S. Pat. No. 5,807,867 (issued Sep. 15, 1998); U.S. Pat. No. 5,886,009 (issued Mar. 23, 1999); U.S. Pat. No. 5,939,433 (issued Aug. 17, 1999); U.S. Pat. No. 5,773,450 (issued Jun. 30, 1998); U.S. Pat. No. 5,744,480 (issued Apr. 28, 1998); U.S. Pat. No. 5,232,929 (issued Aug. 3, 1993); U.S. Pat. No. 5,332,817 (issued Jul. 26, 1994); U.S. Pat. No. 5,122,525 (issued Jun. 16, 1992), U.S. Pat. No. 5,843,966 (issued Dec. 1, 1998); U.S. Pat. No. 5,703,240 (issued Dec. 30, 1997); U.S. Pat. No. 5,719,147 (issued Feb. 17, 1998); and U.S. Pat. No. 5,637,699 (issued Jun. 10, 1997). Each of the foregoing U.S. patents and the foregoing published PCT International Application are incorporated in their entireties herein by reference. The compounds described in said references having NK-1 receptor antagonizing activity can be used in the present invention. However, other NK-1 receptor antagonists can also be used in this invention.

The effective amount of an NK-1 receptor antagonist in combination with a cdk5 inhibitor, for example a compound of formula 1, can generally be determined by a person of ordinary skill. A proposed effective daily dose range for an NK-1 receptor antagonist in combination with a cdk5 inhibitor is from about 0.07 to about 21 mg/kg body weight. The effective amount of the cdk5 inhibitor generally will be between about 0.0001 to about 10 mg/kg body weight. In some instances the amount of NK-1 receptor antagonist and/or the amount of cdk5 inhibitor in the combination may be less than would be required on an individual basis to achieve the same desired effect in treating depression or anxiety.

The subject invention also provides combining a cdk5 inhibitor, such as a compound of formula 1, with a $5HT_{1D}$ receptor antagonist for treatment of depression or anxiety. A $5HT_{1D}$ receptor antagonist, as recited herein, is a substance that antagonizes the $5HT_{1D}$ subtype of serotonin receptor. Any such substance can be used in the present invention as described above in combination with a cdk5 inhibitor, for example a compound of formula 1. Substances having $5HT_{1D}$ receptor antagonizing activity can be determined by those of ordinary skill in the art. For example, $5HT_{1D}$ receptor antagonists are described in WO 98/14433 (International Publication Date Apr. 9, 1998); WO 97/36867 (International Publication Date Oct. 9, 1997); WO 94/21619 (International Publication Date Sep. 29, 1994); U.S. Pat. No. 5,510,350 (issued Apr. 23, 1996); U.S. Pat. No. 5,358,948 (issued Oct. 25, 1994); and GB 2276162 A (published Sep. 21, 1994). These $5HT_{1D}$ receptor antagonists, as well as others, can be used in the present invention. The aforementioned published patent applications and patents are incorporated herein by reference in their entireties.

The effective amount of a $5HT1_D$ receptor antagonist in combination with a cdk5 inhibitor, for example a compound of formula 1, can generally be determined by a person of ordinary skill. A proposed effective daily dose range for a $5HT1_D$ receptor antagonist in combination with a cdk5 inhibitor is from about 0.01 to about 40 mg/kg body weight. The effective daily amount of the cdk5 inhibitor generally will be between about 0.0001 to about 10 mg/kg body weight. In some instances the amount of $5HT1_D$ receptor antagonist and/or the amount of cdk5 inhibitor in the combination may be less than would be required on an individual basis to achieve the same desired effect in treating depression or anxiety.

This invention also provides a pharmaceutical composition and method for treating depression or anxiety in a mammal comprising a cdk5 inhibitor, for example a compound of formula 1, and a SSRI. Examples of SSRIs that can be combined in a method or pharmaceutical composition with cdk5 inhibitors, for example compounds of formula 1 and their pharmaceutically acceptable salts include, but are not limited to, fluoxetine, paroxetine, sertraline, and fluvoxamine. Other SSRIs may be combined or administered in combination with a cdk5 inhibitor, for example a compound of formula 1 or a pharmaceutically acceptable salt thereof. Other antidepressants and/or anxiolytic agents with which a cdk5 inhibitor such as a compound of formula 1 may be combined or administered include WELLBUTRIN, SERZONE and EFFEXOR.

The effective amount of a SSRI in combination with a cdk5 inhibitor, for example a compound of formula 1, can generally be determined by a person of ordinary skill. A proposed effective daily dose range for a SSRI in combination with a cdk5 inhibitor is from about 0.01 to about 500 mg/kg body weight. The effective daily amount of the cdk5 inhibitor generally will be between about 0.0001 to about 10 mg/kg body weight. In some instances the amount of SSRI and/or the amount of cdk5 inhibitor in the combination may be less than would be required on an individual basis to achieve the same desired effect in treating depression or anxiety.

A cdk5 inhibitor, for example a compound of formula 1, or a pharmaceutically acceptable salt thereof, can also be combined with one or more antipsychotic agents, for example a dopaminergic agent, for the treatment of diseases or conditions the treatment of which can be effected or facilitated by altering dopamine neurotransmission, such as schizophrenia. Examples of antipsychotics with which a compound of the invention can be combined include ziprasidone (5-(2-(4-(1,2-benzisothiazol-3-yl)-1-piperazinyl) ethyl)-6-chloro-1,3-dihydro-2H-indol-2-one; U.S. Pat. No. 4,831,031 and U.S. Pat. No. 5,312,925); olanzapine (2-methyl-4-(4-methyl-1-piperazinyl-10H-thieno (2,3b) (1,5)benzodiazepine; U.S. Pat. No. 4,115,574 and U.S. Pat. No. 5,229,382); risperidone (3-[2-[4-(6-fluoro-1,2-benzisoxazol-3-yl)-1-piperidinyl]ethyl]6,7,8,9-tetrahydro-2-methyl-4H-pyrido[1,2-a]pyrimidin-4-one; U.S. Pat. No. 4,804,663); L-745870 (3-(4-(4-chlorophenyl)piperazin-1-yl)methyl-1H-pyrrolo(2,3-b)pyridine; U.S. Pat. No. 5,432,177); sonepiprazole (S-4-(4-(2-(isochroman-1-yl)ethyl)piperazin-1-yl)benzenesulfonamide; U.S. Pat. No. 5,877,317); RP 62203 (fananserin; 2-(3-(4-(4-fluorophenyl)-1-piperazinyl)propyl) naphtho(1,8-c,d)isothiazole-1,1-dioxide; U.S. Pat. No. 5,021,420); NGD 941 (U.S. Pat. No. 5,633,376 and U.S. Pat. No. 5,428,165); balaperidone ((1α,5α,6α)-3-(2-(6-(4-fluorophenyl)-3-azabicyclo(3.2.0)hept-3-yl)ethyl)-2,4(1H,3H)-quinazolinedione; U.S. Pat. No. 5,475,105); flesinoxan ((+)-4-fluoro-N-[2-[4-5-(2-hydroxymethyl-1,4-benzodioxanyl)]-1-piperazinyl]ethyl]benzamide; U.S. Pat. No. 4,833,142); and gepirone (4,4-dimethyl-1-(4-(4-(2-pyrimidinyl)-1-piperazinyl)butyl)-2,6-piperidinedione; U.S. Pat. No. 4,423, 049). The patents recited above in this paragraph are each incorporated herein by reference in their entireties. The effective daily amount of the cdk5 inhibitor generally will be between about 0.0001 to about 10 mg/kg body weight. The amount of any of the aforementioned antipsychotic agents contemplated for use in combination with a cdk5 inhibitor, for example a compound of formula 1, is generally the amount known in the art to be useful for treating psychotic conditions. However, in some instances, the amount of the antipsychotic and/or the amount of cdk5 inhibitor in the combination may be less than would be required on an individual basis to achieve the same desired effect in treating depression or anxiety. It is furthermore to be understood that the present invention also encompasses combining a cdk5 inhibitor, for example a compound of formula 1 with antipsychotic or dopaminergic other than those in the aforementioned list.

A proposed amount for sonepiprazole in the above-described combination with a cdk5 inhibitor, for example a compound of formula 1, is from about 0.005 to about 50 mg/kg body weight of the patient per day. A proposed amount of RP 62203 in such combination is from about 0.20 to about 6 mg/kg body weight of the patient per day. A proposed amount of NGD 941 in such combination is from about 0.1 to about 140 mg/kg of body weight per day. A proposed amount of balaperidone in such combination is from about 1 to about 100 mg/kg body weight per day. A proposed amount of flesinoxan in such combination is from about 0.02 to about 1.6 mg/kg body weight per day. A proposed amount for gepirone in such combination is from about 0.01 to about 2 mg/kg body weight per day. A proposed amount of L-745870 in such combination is from about 0.01 to about 250 mg/kg body weight per day, preferably from about 0.05 to about 100 mg/kg body weight per day. A proposed amount of risperidone in such combination is from about 0.05 to about 50 mg/kg body weight per day. A proposed amount of olanzapine in such combination is from about 0.0005 to about 0.6 mg/kg body weight per day. A proposed amount of ziprasidone in such combination is from about 0.05 to about 10 mg/kg body weight per day. In some instances for each of the aforementioned combinations, however, the amount of each specific ingredient in the combination may be less than would be required on an individual basis to achieve the same desired effect in treating a psychotic condition.

This invention also provides a pharmaceutical composition and method for treating Alzheimer's disease, mild cognitive impairment, or age-related cognitive decline comprising a cdk5 inhibitor, for example a compound of formula 1, and an acetylcholinesterase inhibitor. Acetylcholinesterase inhibitors are known in the art, and any such acetylcholinesterase inhibitor can be used in the above-described pharmaceutical composition or method. Examples of acetylcholinesterase inhibitors that can be used in this invention are ARICEPT (donepezil; U.S. Pat. No. 4,895,841); EXELON (rivastigmine ((S)-[N-ethyl-3-[1-(dimethylamino)ethyl]phenyl carbamate); U.S. Pat. No. 5,603,176 and U.S. Pat. No. 4,948,807); metrifonate ((2,2,2-trichloro-1-hydroxyethyl)phosphonic acid dimethyl ester; U.S. Pat. No. 2,701,225 and U.S. Pat. No. 4,950,658); galantamine (U.S. Pat. No. 4,663,318); physostigmine (Forest, USA); tacrine (1,2,3,4-tetrahydro-9-acridinamine; U.S. Pat. No. 4,816,456); huperzine A (5R-(5α,9β,11E))-5-amino-11-ethylidene-5,6,9,10-tetrahydro-7-methyl-5,9-methaneocyclooocta(b)pyridin-2-(1H )-one); and icopezil (5,7-dihydro-3-(2-(1-(phenylmethyl)-4-piperidinyl)ethyl)-6H-pyrrolo(3, 2-f)-1,2-benzisoxazol-6-one; U.S. Pat. No. 5,750,542 and WO 92/17475). The patents and patent applications recited above in this paragraph are herein incorporated by reference in their entireties.

The effective amount of an acetylcholinesterase inhibitor in combination with a cdk5 inhibitor, for example a compound of formula 1, can generally be determined by a person of ordinary skill. A proposed effective daily dose range for an acetylcholinesterase inhibitor in combination with a cdk5 inhibitor is from about 0.01 to about 10 mg/kg body weight. The effective daily amount of the cdk5 inhibitor generally will be between about 0.0001 to about 10 mg/kg body weight. In some instances the amount of acetylcholinesterase inhibitor and/or the amount of cdk5 inhibitor in the combination may be less than would be required on an individual basis to achieve the same desired effect in treating Alzheimer's disease, mild cognitive impairment, or age-related cognitive decline.

The present invention also provides for combining a cdk5 inhibitor with neuroprotectants, for example NMDA receptor antagonists, for treatment of Huntington's disease, stroke, spinal cord trauma, traumatic brain injury, multiinfarct dementia, epilepsy, amyotrophic lateral sclerosis, pain, viral induced dementia for example AIDS induced dementia, migraine, hypoglycemia, urinary incontinece, brain ischemia, multiple sclerosis, Alzheimer's disease, senile dementia of the Alzheimer's type, mild cognitive impairment, age-related cognitive decline, emesis, corticobasal degeneration, dementia pugilistica, Down's syndrome, myotonic dystrophy, Niemann-Pick disease, Pick's disease, prion disease with tangles, progessive supranuclear palsy, lower lateral sclerosis, or subacute sclerosing panencephalistis. Examples of NMDA receptor antagonists that can be used in the present invention include (1S,2S)-1-(4-hydroxyphenyl)-2-(4-hydroxy-4-phenylpiperidin-1-yl)-1-propanol (U.S. Pat. No. 5,272,160), eliprodil (U.S. Pat. No. 4,690, 931), and gavestenel (U.S. Pat. No. 5,373,018). Other NMDA receptor antagonists, which can also be used in the present invention, are described in U.S. Pat. No. 5,373,018; U.S. Pat. No. 4,690,931; U.S. Pat. No. 5,272,160; U.S. Pat. No. 5,185,343; U.S. Pat. No. 5,356,905;. U.S. Pat. No. 5,744,483; WO 97/23216; WO 97/23215; WO 97/23214; WO 96/37222; WO 96/06081; WO 97/23458; WO 97/32581; WO 98/18793; WO 97/23202; and U.S. Ser. No. 08/292,651 (filed Aug. 18, 1994). The aforementioned patents and patent applications are each hereby incorporated by reference in their entireties.

The effective daily amount of the cdk5 inhibitor in the combination with an NMDA receptor antagonist generally will be between about 0.0001 to about 10 mg/kg body weight. The amount of the NMDA receptor antagonist contemplated for use in combination with a cdk5 inhibitor, for example a compound of formula 1, for treatment of any of the aforementioned disorders, for example Alzheimer's disease, is generally within the range of from about 0.02 mg/kg/day to about 10 mg/kg/day. However, in some instances, the amount of the NMDA antagonist and/or the amount of cdk5 inhibitor in the combination may be less than would be required on an individual basis to achieve the same desired effect in treating said disorders.

The subject invention also provides for combining a cdk5 inhibitor with certain substances capable of treating a stroke or traumatic brain injury, such as TPA, NIF, or potassium channel modulators, for example BMS-204352. Such combinations are useful for treating neurodegenerative disorders such as stroke, spinal cord trauma, traumatic brain injury, multiinfarct dementia, epilepsy, pain, Alzheimer's disease, and senile dementia, for example.

For the above-described combination therapies and pharmaceutical compositions, the effective amounts of the compound of the invention and of the other agent can generally be determined by those of ordinary skill in the art, based on the effective amounts for the compounds described herein and those known or described for the other agent known in the art, for example the amounts described in the above-recited patents and patent application incorporated herein. The formulations and routes of administration for such therapies and compositions can be based on the information described herein for compositions and therapies comprising a compound of the invention as the sole active agent and on information provided for the other agent in combination therewith.

A specific compound of formula 1 can be determined to inhibit cdk2, cdk5, or GSK-3 using biological assays known to those of ordinary skill in the art, for example the assays described below.

The specific activity of a compound of formula 1 for inhibition of cdk5 or cdk2 can, for example, be ascertained by means of the following assays using materials available to those of ordinary skill in the art:

Enzyme activities can be assayed as the incorporation of [33P] from the gamma phosphate of [33P]ATP (Amersham, cat. no. AH-9968) into biotinylated peptide substrate PKT-PKKAKKL. In such an assay, reactions are carried out in a buffer containing 50 mM Tris-HCl, pH 8.0; 10 mM MgCl2, 0.1 mM Na3VO4, and 1 mM DTT. The final concentration of ATP is about 0.5 uM (final specific radioactivity of 4uCi/nmol), and the final concentration of substrate 0.75 uM. Reactions, initiated by the addition of either cdk5 and activator protein p25 or cdk2 and activator cyclin E, may be carried out at room temperature for about 60 minutes. Reactions are stopped by addition of 0.6 volume of buffer containing (final concentrations): 2.5 mM EDTA, 0.05% Triton-X 100, 100 uM ATP, and 1.25 mg/ml streptavidin coated SPA beads (Amersham cat. no. RPNQ0007). Radioactivity associated with the beads is quantified by scintillation counting.

The specific activity of a compound of formula 1 for inhibition of GSK-3 can be determined in both cell-fee and cell-based assays, both of which are described in the art (see, for example, WO 99/65897). A cell-free assay can be carried out in general by incubating GSK-3 with a peptide substrate, radiolabeled ATP (such as, for example, $\gamma^{33}$P- or $\gamma^{32}$-P-ATP, both available from Amersham, Arlington Heights, Ill.), magnesium ions, and the compound to be assayed. The mixture is incubated for a period of time to allow incorporation of radiolabeld phosphate into the peptide substrate by GSK-3 activity. The reaction mixture is washed to remove unreacted radiolabeled ATP, typically after first transferring all or a portion of the enzyme reaction mixture to a well that contains a uniform amount of a ligand that is capable of binding to the peptide substrate. The amount of $^{33}$P or $^{32}$P remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, derived from the CREB DNA binding protein, described in Wang, et al., *Anal. Biochem.*, 220:397–402 (1994). Purified GSK-3 for an assay may, for example, be obtained from cells transfected with a human GSK-3β expression plasmid as described in, for example Stambolic, et al., *Current Biology* 6:1664–68 (1996). WO 99/65897; Wang, et al., and Stambolic, et al. are incorporated in their entireties herein by reference.

Another example of a GSK-3 assay, similar to the one described in the preceding paragraph is as follows: Enzyme activities are assayed as the incorporation of [33P] from gamma phosphate of [33P]ATP (Amersham, cat. No. AH-9968) into biotinylated peptide substrate PKTP-KKAKKL. Reactions are carried out in a buffer containing 50 mM Tris-HCl, pH 8.0; 10 mM MgCl$_2$, 0.1 mM Na$_3$VO$_4$, and 1 mM DTT. The final concentration of ATP is 0.5 μM (final specific radioactivity of 4 μCi/nmol), and the final concentration of substrate is 0.75 μM. Reactions, initiated by the addition of enzyme, are carried out at room temperature for about 60 minutes. Reactions are stopped by addition of 0.6 volume of buffer containing (final concentrations): 2.5 mM EDTA, 0.05%Triton-X 100, 100 μM ATP, and 1.25 mg/ml streptavidin coated SPA beads (Amersham cat. No. RPNQ0007). Radioactivity associated with the beads is quantified by scintillation counting.

All of the title compounds of the following Examples had an $IC_{50}$ inhibiting peptide substrate phosphorylation of less than about 50 μM when assayed for cdk5 inhibition according to the preceding assay.

Several of the title compounds of the following Examples were assayed for GSK-3 inhibition using an assay such as that described above, and all tested had an $IC_{50}$ for inhibition of GSK-3β of less than about 50 μM.

The following Examples illustrate the present invention. It is to be understood, however, that the invention, as fully described herein and as recited in the claims, is not intended to be limited by the details of the following Examples.

EXAMPLES

Preparation 1

1-Cyclobutyl-4-nitro-1H-imidazole 1,4-Dinitroimidazole (237 mg, 1.5 mmol, *J. Phys. Chem.* 1995, 99, 5009–5015) was added to a solution of cyclobutylamine (107 mg, 1.5 mmol) in methanol (10 mL) at 23° C. The reaction mixture was stirred for 16 h, then the solvent was removed in vacuo and the resulting residue was purified by silica gel chromatography (1:1 hexanes-ethyl acetate) to afford 230 mg (92% yield) of 1-cyclobutyl-4-nitro-1H-imidazole; 1H NMR (400 MHz, CDCl$_3$) δ 7.81 (s, 1H), 7.45 (s, 1H), 4.64 (m, 1H), 2.6 (m, 2H), 2.4 (m, 2H), 2.0 (m, 2H); MS (AP/CI): 168.2 (M+H)$^+$. Note: 1,4-Dinitroimidazole is a highly energetic, semi-stable substance and should be stored in a freezer at all times it is not in use. Thermodynamic measurements have shown that it can potentially generate enough energy at 35° C. under adiabatic conditions to violently explode. Extreme caution should be exercised at all times using this material.

Preparation 2

1-Cyclopentyl-4-nitro-1H-imidazole

This reaction was carried out using the procedure for Preparation 1 with cyclopentyl amine and 1,4-dinitroimidazole to afford 205 mg (75% yield) of 1-cyclopentyl-4-nitro-1H-imidazole; 1H NMR (400 MHz, CDCl$_3$) δ 7.77 (s, 1H), 7.45 (s, 1H), 4.49 (m, 1H), 2.25 (m, 2H), 2.0–1.7 (m, 6H); MS (AP/CI): 182.2 (M+H)$^+$.

Preparation 3

4-Nitro-1-(cis-3-phenyl-cyclobutyl)-1H-imidazole

This reaction was carried out using the procedure for Preparation 1 with cis-3-phenylcyclobutylamine (*J. Med. Pharm. Chem.* 1960, 2, 687–691; *ACIEE* 1981, 20, 879–880) and 1,4-dinitroimidazole to afford 46 mg (46% yield) of 4-nitro-1-(cis-3-phenyl-cyclobutyl)-1H-imidazole; 1H NMR (300 MHz, CDCl$_3$) δ 7.9 (s, 1H), 7.55 (s, 1H), 7.4–7.2 (m, 5H), 4.73 (m, 1H), 3.48 (m, 1H), 3.12 (m, 2H), 2.54 (m, 2H); MS (AP/CI): 244 (M+H)$^+$.

Example 1

N-(1-Cyclobutyl-1H-imidazol-4-yl)-2-quinolin-6-yl-acetamide

To a Parr hydrogenation bottle was added 1-cyclobutyl-4-nitro-1H-imidazole (Preparation 1, 150 mg, 0.9 mmol) and ethyl acetate (10 mL), followed by 10% Pd on carbon (250 mg). The reaction mixture was placed on a Parr hydrogenation apparatus and was reacted for 6 h under 50 psi H$_2$ at 23° C. The contents of the bottle were filtered through a short pad of celite and were rinsed with dry methylene chloride (25 mL) into a flame-dried flask under nitrogen. Et$_3$N (626 uL, 4.5 mmol) was added and the reaction solution was cooled to −10° C. 6-Quinolylacetic acid (168 mg, 0.9 mmol) and tripropylphosphonic anhydride (530 uL, 1.7 M solution in ethyl acetate) were then added and the mixture was stirred at −10° C. for 2 h. The solution was diluted with methylene chloride (50 mL) and washed with water (2×). The aqueous layer was extracted with methylene chloride (3×) and the organic layers were combined and washed with brine (1×). The solvent was removed in vacuo, the residue was adsorbed onto silica gel and chromatographed using the Biotage Flash 12 system with SIM attachment (40:1 methylene chloride-methanol) to afford 130 mg (47% yield) of N-(1-cyclobutyl-1H-imidazol-4-yl)-2-quinolin-6-yl-acetamide (the title compound); 1H NMR (300 MHz, CDCl$_3$) δ 9.48 (s, 1H), 8.87 (dd, J=1.6, 4.3 Hz, 1H), 8.11 (m, 2H), 7.76 (d, J=1.8 Hz, 1H), 7.67 (dd, J=2.0, 8.7 Hz, 1H), 7.44 (d, J=1.6 Hz, 1H), 7.38 (m, 1H), 7.25 (d, J=1.6 Hz, 1H), 4.5 (m, 1H), 3.90 (s, 2H), 2.4 (m, 2H), 2.3 (m, 2H), 1.85 (m, 2H); MS (AP/CI): 307.1 (M+H)$^+$.

Example 2

N-(1-Cyclopentyl-1H-imidazol-4-yl)-2-(4-methoxy-phenyl)-acetamide

The procedure for Example 1 was carried out with para-methoxy-phenylacetic acid and 1-cyclopentyl-4-nitro-1H-imidazole (Preparation 2) to prepare N-(1-cyclopentyl-1H-imidazol-4-yl)-2-(4-methoxy-phenyl)-acetamide in 32% yield (26.5 mg); 1H NMR (400 MHz, CDCl$_3$) δ 8.54 (s, 1H), 7.35 (s, 1H), 7.24 (m, 2H), 6.87 (d, J=1.7 Hz), 4.36 (m, 1H), 3.78 (s, 3H), 3.64 (s, 2H), 2.1 (m, 2H), 1.8 (m, 4H), 1.6 (m, 2H); MS (AP/CI): 300.3 (M+H)$^+$.

Example 3

N-[1-(cis-3-Phenyl-cyclobutyl)-1H-imidazol-4-yl]-2-quinolin-6-yl-acetamide

The procedure for Example 1 was carried out with 6-quinolylacetic acid and 4-nitro-1-(cis-3-phenyl-cyclobutyl)-1H-imidazole (Preparation 3) to prepare N-[1-(cis-3-phenyl-cyclobutyl)-1H-imidazol-4-yl]-2-quinolin-6-yl-acetamide in 38% yield; 1H NMR (300 MHz, CDCl$_3$) δ 8.93 (m, 1H), 8.12 (m, 2H), 7.79 (d, J=1.5 Hz, 1H), 7.71 (m, 1H), 7.55 (d, J=1.5 Hz, 1H), 7.41 (dd, J=4.3, 8.4 Hz, 1H), 7.37–7.22 (m, 5H), 4.57 (m, 1H), 3.96 (s, 2H), 3.33 (m, 1H), 2.95 (m, 2H), 2.49 (m, 2H); MS (AP/CI): 383.0 (M+H)$^+$.

Example 4

(1-Cyclobutyl-1H-imidazol-4-yl)-carbamic acid phenyl ester

A Parr hydrogenation bottle was charged with 1-cyclobutyl-4-nitro-1H-imidazole (Preparation 1, 3 g, 18 mmol) and ethyl acetate (70 mL) followed by 10% Pd on carbon (1.2 g) under a nitrogen atmosphere. The mixture was hydrogenated for 6 h under 50 psi H$_2$ at 23° C. The mixture was then filtered through a pad of celite which was rinsed with dry methylene chloride (140 mL) into a flame-dried flask. The resulting solution was cooled to −78° C. and diisopropyl-ethylamine (2.3 g, 18 mmol) was added followed by the dropwise addition of phenylchloroformate (2.5 g, 16.2 mmol). After 30 min, methanol (9 mL) containing acetic acid (1.8 mmol) was added. The reaction mixture was transferred to a separatory funnel, was diluted with ethyl acetate (200 mL), and was washed with water (2×). The aqueous layers were extracted with ethyl acetate (2×10 mL). The organic layers were combined, were washed with brine (2×), and were then dried (MgSO$_4$), filtered, and concentrated in vacuo. The crude product was adsorbed onto silica gel and was purified by silica gel chromatography (1:1 hexanes-ethyl acetate) to afford 3 g (65% yield) of (1-cyclobutyl-1H-imidazol-4-yl)-carbamic acid phenyl ester; 1H NMR (400 MHz, CDCl$_3$) δ 7.4–7.3 (m, 2H), 7.22–7.18 (m, 3H), 4.5 (m, 1H), 2.46–2.30 (m, 4H), 1.83 (m, 2H); MS (AP/CI): 258.2 (M+H)$^+$.

Example 5

1-(1-Cyclobutyl-1H-imidazol-4-yl)-3-isoquinolin-5-yl-urea

To a 1 dram vial with septa screw cap was added (1-cyclobutyl-1H-imidazol-4-yl)-carbamic acid phenyl ester (Example 4, 50 mg, 0.19 mmol), 5-aminoisoquinoline (30 mg, 0.21 mmol), and 1:1 dioxane-DMF (1 mL). The reaction mixture was heated at 70° C. for 2 h. The reaction mixture was adsorbed onto silica gel and was purified by silica gel chromatography (40:1 chloroform-methanol) to afford 30 mg (52% yield) of 1-(1-cyclobutyl-1H-imidazol-4-yl)-3-isoquinolin-5-yl-urea; 1H NMR (400 MHz, CD$_3$OD) δ 9.21 (d, J=1.7 Hz, 1H), 8.45 (d, J=6.2 Hz, 1H), 8.24 (d, J=7.5 Hz, 1H), 7.98 (d, J=5.4 Hz, 1H), 7.84 (dd, J=2.3, 8.3 Hz, 1H), 7.66 (m, 1H), 7.54 (s, 1H), 7.12 (brs, 1H), 4.66 (m, 1H), 2.5–2.3 (m, 4H), 1.9 (m, 2H); MS (AP/CI): 308.0 (M+H)$^+$.

Preparation 4

N-[1-(cis-3-Azido-cyclobutyl)-1H-imidazol-4-yl]-2-naphthalen-1-yl-acetamide

Step 1

3-Benzyloxycyclobutylamine (43.4 g, 245 mmol, *Chem. Ber.* 1957, 90, 1424–1432) was dissolved in methanolic hydrogen chloride (saturated, 450 mL), then 10% Pd on carbon (4 g) was added. The mixture was hydrogenated at 50 psi H$_2$ for 6 h. The mixture was filtered and concentrated in vacuo to give ca. 35 g of an oil. The oil was taken up in methanol (600 mL), was cooled to 0° C., and was treated with potassium hydroxide (13.7 g, 245 mmol). When the pH=10, a solution of 1,4-dinitroimidazole (42.7 g, 270 mmol) in methanol (200 mL) (prepared by dissolving 1,4-dinitroimidazole in methanol at 0° C.) was added. (Note: 1,4-Dinitroimidazole is a highly energetic, semi-stable substance and should be stored in a freezer at all times it is not in use. Thermodynamic measurements have shown that it can potentially generate enough energy at 35° C. under adiabatic conditions to violently explode. Extreme caution should be exercised at all times using this material.) The resulting orange suspension was then allowed to slowly warm to 23° C. overnight. The solvent was removed in vacuo and the resulting residue was purified by passage through a large plug of silica gel (20:1 chloroform-methanol) to afford 19 g (42% yield) of 3-(4-nitro-imidazol-1-yl)-cyclobutanol as a 1:1 mixture of cis-trans isomers; 1H NMR (400 MHz, CD$_3$OD) δ 8.29 (s, 1H), 8.27 (s, 1H), 7.84 (s, 1H), 7.81 (s, 1H), 5.02 (m, 1H), 4.53 (m, 1H), 4.37 (m, 1H), 4.10 (m, 1H), 2.95 (m, 2H), 2.7 (m, 2H), 2.5 (m, 2H), 2.3 (m, 2H); MS (AP/CI): 184.0 (M+H)$^+$.

Step 2

3-(4-nitro-imidazol-1-yl)-cyclobutanol (Preparation 4, Step 1; 4 g, 22 mmol) was treated with Et$_3$N (7.7 mL, 55 mmol) in methylene chloride (150 mL) followed by p-toluenesulfonyl chloride (TsCl) (5 g, 26.4 mmol) and 4-N,N- dimethylaminopyridine (DMAP) (268 mg, 2.2 mmol). The resulting mixture was stirred at room temperature for 24 h. Analysis by thin layer chromatography showed two new spots. The reaction mixture was diluted with methylene chloride and was washed with water (1×) and brine (1×). The organic layer was dried (MgSO$_4$), filtered, and concentrated in vacuo. Purification by silica gel chromatography (1:1 to 2:1 hexanes-ethyl acetate) allowed for separation of the trans and cis diastereomers. The first spot to elute (high Rf) was the trans-isomer, trans-toluene-4-sulfonic acid 3-(4-nitro-imidazol-1-yl)-cyclobutyl ester (2.7 g, 37% yield); 1H NMR (400 MHz, CDCl$_3$) δ 7.79 (s, 1H), 7.77 (m, 2H), 7.44 (d, J=1.7 Hz, 1H), 7.36 (dd, J=0.5, 8.0 Hz, 2H), 5.034 (m, 1H), 4.94 (m, 1H), 2.9 (m, 2H), 2.7 (m, 2H); MS (AP/CI): 338.1 (M+H)$^+$. The second spot to elute was the cis-isomer, cis-toluene-4-sulfonic acid 3-(4-nitro-imidazol-1-yl)-cyclobutyl ester (2.9 g, 39% yield); 1H NMR (400 MHz, CDCl$_3$) δ 7.8 (m, 3H), 7.43 (d, J=1.4 Hz, 1H), 7.36 (dd, J=0.6, 8.5 Hz, 2H), 4.74 (m, 1H), 4.30 (m, 1H), 3.05 (m, 2H), 2.6–2.5 (m, 2H), 2.45 (s, 3H); MS (AP/CI): 338.1 (M+H)$^+$. Relative configurations were determined by the measurement of nuclear Overhauser effects.

Step 3 trans-Toluene-4-sulfonic acid 3-(4-nitro-imidazol-1-yl)-cyclobutyl ester (Preparation 4, Step 2; 590 mg, 1.75 mmol) was mixed with 10% Pd on carbon (500 mg) in ethyl acetate (30 mL). The mixture was then reacted under 50 psi H$_2$ at room temperature for 6 h. The mixture was filtered through celite into a flame-dried flask which was kept under a nitrogen atmosphere. Et$_3$N (1.22 mL, 8.75 mmol) was added followed by 1-naphthylacetic acid (326 mg, 1.75 mmol) and tripropylphosphonic anhydride (1.1 mL, 1.7 M solution in ethyl acetate, 1.75 mmol). The mixture was stirred at room temperature for 1 h and was then diluted with ethyl acetate and was washed with water and brine. The organic layer was dried (MgSO$_4$), was filtered, and was concentrated in vacuo. The resulting residue was purified by silica gel chromatography (50:1 chloroform-methanol) to afford 600 mg (72% yield) of trans-toluene-4-sulfonic acid 3-[4-(2-naphthalen-1-yl-acetylamino)-imidazol-1-yl]-cyclobutyl ester; 1H NMR (400 MHz, CDCl$_3$) δ 7.9 (m, 2H), 7.85 (m, 2H), 7.76 (d, J=8.3 Hz, 2H), 7.48 (m, 2H), 7.42 (m, 2H), 7.33 (m, 2H), 7.04 (s, 1H), 4.96 (m, 1H), 4.73 (m, 1H), 2.7 (m, 4H), 2.44 (s, 3H); MS (AP/CI): 476.2 (M+H)+.

Step 4 trans-Toluene-4-sulfonic acid 3-[4-(2-naphthalen-1-yl-acetylamino)-imidazol-1-yl]-cyclobutyl ester (Preparation 4, Step 3; 593 mg, 1.25 mmol) was mixed with sodium azide (813 mg, 12.5 mmol) in ethanol (15 mL), water (5 mL), and chloroform (5 mL). The mixture was then heated at reflux with stirring for 96 h. The solvent was removed in vacuo and the residue was diluted with water and was extracted with methylene chloride. The organic layer was dried (MgSO$_4$), filtered, and was concentrated in vacuo. Purification by silica gel chromatography (50:1 chloroform-methanol) afforded 340 mg (79% yield) of N-[1-(cis-3-azido-cyclobutyl)-1H-imidazol-4-yl]-2-naphthalen-1-yl-acetamide; 1H NMR (400 MHz, CDCl$_3$) δ 8.41 (s, 1H), 7.98 (d, J=6.4 Hz, 1H), 7.87 (m, 1H), 7.82 (m, 1H), 7.5 (m, 2H), 7.45 (m, 3H), 7.08 (d, J=1.7 Hz, 1H), 4.2 (m, 3H), 3.75 (m, 1H), 2.85 (m, 2H), 2.35 (m, 2H); MS (AP/CI): 347.2 (M+H)+.

Example 6

N-[1-(cis-3-Amino-cyclobutyl)-1H-imidazol-4-yl]-2-naphthalen-1-yl-acetamide

N-[1-(cis-3-azido-cyclobutyl)-1H-imidazol-4-yl]-2-naphthalen-1-yl-acetamide (Preparation 4, Step 4; 330 mg, 0.95 mmol) was treated with triphenylphosphine (301 mg, 1.15 mmol) in tetrahydrofuran (10 mL) and water (1 mL) at 23° C. The solution was stirred at room temperature for 18 h. The solvent was removed in vacuo and the resulting residue was purified by silica gel chromatography (20:1:0.5 chloroform-methanol-ammonium hydroxide) to afford 289 mg (95% yield) of N-[1-(cis-3-amino-cyclobutyl)-1H-imidazol-4-yl]-2-naphthalen-1-yl-acetamide; 1H NMR (400 MHz, CD3OD) δ 8.05 (d, J=7.5 Hz, 1H), 7.87 (d, J=7.9 Hz, 1H), 7.79 (d, J=9.0 Hz, 1H), 7.45 (m, 5H), 7.35 (s, 1H), 4.26 (m, 1H), 4.16 (s, 2H), 3.29 (m, 2H), 3.16 (m, 1H), 2.75 (m, 2H), 2.1 (m, 2H); MS (AP/CI): 321.3 (M+H)+.

Example 7a

6-Methyl-pyridine-2-carboxylic acid {cis-3-[4-(2-naphthalen-1-yl-acetylamino)-imidazol-1-yl]-cyclobutyl}-amide A solution of 6-methylpicolinic acid (9.4 mg, 0.07 mmol) in methylene chloride was treated with 1-(3-dimethylaminopropyl)-3-ethylcarbodiimide hydrochloride (84 mg) and DMAP (2 mg) at 23° C. After stirring for 10 min, N-[1-(cis-3-amino-cyclobutyl)-1H-imidazol-4-yl]-2-naphthalen-1-yl-acetamide (Example 6, 20 mg, 0.06 mmol), was added. The resulting mixture was then stirred for 3 h. Water was added, the solution was made neutral with aqueous NaOH and was extracted with ethyl acetate. The organic layer was dried (MgSO$_4$), filtered, and concentrated in vacuo. Purification by silica gel chromatography (20:1 CHCl$_3$-MeOH) gave 26 mg (95% yield) of 6-methyl-pyridine-2-carboxylic acid {3-[4-(2-naphthalen-1-yl -acetylamino)-imidazol-1-yl]-cyclobutyl}-amide; 1H NMR (400 MHz, CDCl$_3$) δ 9.15 (s, 1H), 8.28 (d, J=8.3 Hz, 1H), 8.01 (d, J=7.5 Hz, 1H), 7.96 (d, J=7.5 Hz, 1H), 7.97 (d, J=7.5 Hz, 1H), 7.81 (dd, J=2.4, 6.6 Hz, 1H), 7.72 (m, 1H), 7.5 (m, 5H), 7.2 (m, 1H), 7.16 (s, 1H), 4.45 (m, 1H), 4.25 (m, 1H), 4.18 (s, 2H), 2.98 (m, 2H), 2.60 (s, 3H), 2.40 (m, 2H); MS (AP/CI): 440.3 (M+H)+.

Example 7b

1H-Imidazole-4-carboxylic acid {cis-3-[4-(2-naphthalen-1-yl-acetylamino)-imidazol-1-yl]-cyclobutyl}-amide title compound was prepared analogously to Example 7a; 1H NMR (400 MHz, CD3OD) δ 8.06 (d, J=7.9 Hz, 1H), 7.87 (m, 1H), 7.80 (d, J=7.5 Hz, 1H), 7.7 (s, 1H), 7.64 (s, 1H), 7.5 (m, 6H), 4.44 (m, 1H), 4.32 (m, 1H), 4.18 (s, 2H), 2.9 (m, 2H), 2.45 (m, 2H); MS (AP/CI): 415.3 (M+H)+.

Example 7c

6-Hydroxy-pyridine-2-carboxylic acid {cis-3-[4-(2-naphthalen-1-yl-acetylamino)-imidazol-1-yl]-cyclobutyl}-amide The title compound was prepared analogously to Example 7a; 1H NMR (400 MHz, CD3OD) δ 8.02 (d, J=7.9 Hz, 1H), 7.84 (d, J=7.9 Hz, 1H), 7.79 (d, J=7.5 Hz, 1H), 7.65 (s, 1H), 7.60 (m, 1H), 7.45 (m, 6H), 7.14 (brs, 1H), 6.71 (d, J=8.7 Hz, 1H), 4.4 (m, 1H), 4.32 (m, 1H), 4.17 (s, 2H), 2.93 (m, 2H), 2.5 (m, 2H); MS (AP/CI): 442.3 (M+H)+.

Example 7d

3-Methyl-pyridine-2-carboxylic acid {cis-3-[4-(2-naphthalen-1-yl-acetylamino)-imidazol-1-yl]-cyclobutyl}-amide The title compound was prepared analogously to Example 7a; 1H NMR (CD3OD, 400 MHz) δ 8.39 (d, J=4.2 Hz, 1H), 8.06 (d, J=8.3 Hz, 1H), 7.87 (d, J=7.5 Hz, 1H), 7.80 (d, J=7.5 Hz, 1H), 7.69 (d, J=7.9 Hz, 1H), 7.5 (m, 7H), 4.5 (m, 1H), 4.3 (m, 1H), 4.17 (s, 2H), 2.92 (m, 2H), 2.54 (s, 3H), 2.46 (m, 2H); MS (AP/CI): 440.3 (M+H)+.

Example 7e

2-Pyridin-3-yl-thiazole-4-carboxylic acid {cis-3-[4-(2-naphthalen-1-yl-acetylamino)-imidazol-1-yl]-cyclobutyl}-amide The title compound was prepared analogously to Example 7a; 1H NMR (400 MHz, CD3OD) 9.21 (d, J=2.5 Hz, 1H), 8.61 (d, J=5.0 Hz, 1H), 8.41 (dd, J=1.7, 7.9 Hz, 1H), 8.26 (s, 1H), 8.06 (d, J=7.9 Hz, 1H), 7.86 (d, J=7.5 Hz, 1H), 7.79 (d, J=7.9 Hz, 1H), 7.5 (m, 7H), 4.44 (m, 2H), 4.17 (s, 2H), 2.9 (m, 2H), 2.6 (m, 2H); MS (AP/CI): 509.3 (M+H)+.

Example 7f

6-{cis-3-[4-(2-Naphthalen-1-yl-acetylamino)-imidazol-1-yl]-cyclobutylcarbamoyl}-nicotinic acid Methyl Ester The title compound was prepared analogously to Example 7a; 1H NMR (400 MHz, CD3OD/CDCl3) δ 9.15 (d, J=1.6 Hz, 1H), 9.12 (d, J=8.0 Hz, 1H), 8.45 (dd, J=2.0, 8.4 Hz, 1H), 8.16 (d, J=8.0 Hz, 1H), 8.02 (d, J=8.4 Hz, 1H), 7.85 (d, J=8.0 Hz, 1H), 7.80 (d, J=7.8 Hz, 1H), 7.48 (m, 6H), 4.45 (m, 2H), 3.96 (s, 3H), 2.94 (m, 2H), 2.58 (m, 2H); MS (AP/CI): 484.3 (M+H)+.

Example 7g

Pyrazine-2-carboxylic acid {cis-3-[4-(2-naphthalen-1-yl-acetylamino)-imidazol-1-yl]-cyclobutyl}-amide The title compound was prepared analogously to Example 7a; 1H NMR (400 MHz, CD3OD) δ 9.23 (d, J=2.0 Hz, 1H), 9.03 (d, J=8.0 Hz, 1H), 8.73 (d, J=2.4 Hz, 1H), 8.63 (d, J=1.6, 2.4 Hz, 1H), 8.02 (d, J=8.4 Hz, 1H), 7.85 (d, J=8.0 Hz, 1H), 7.79 (d, J=8.0 Hz, 1H), 7.49 (m, 6H), 4.44 (m, 2H), 4.16 (s, 2H), 2.95 (m, 2H), 2.56 (m, 2H); MS (AP/CI): 427.3 (M+H)+.

Example 7h

N-{cis-3-[4-(2-Naphthalen-1-yl-acetylamino)-imidazol-1-yl]-cyclobutyl}-benzamide The title compound was prepared analogously to Example 7a; 1H NMR (400 MHz, CD3OD) δ 8.05 (d, J=8.3 Hz, 2H), 7.99 (d, J=7.1 Hz, 1H), 7.86 (d, J=7.5 Hz, 1H), 7.80 (d, J=7.1 Hz, 2H), 7.45 (m, 8H), 4.47 (m, 1H), 4.37 (m, 1H), 4.17 (s, 2H), 2.90 (m, 2H), 2.47 (m, 2H); MS (AP/CI): 425.0 (M+H)+.

Example 7i

5-Methyl-pyrazine-2-carboxylic acid {cis-3-[4-(2-naphthalen-1-yl-acetylamino)-imidazol-1-yl]-cyclobutyl}-amide The title compound was prepared analogously to Example 7a; 1H NMR (400 MHz, CD3OD) δ 9.07 (d, J=1.2 Hz, 1H), 8.5 (d, J=0.8 Hz, 1H), 8.02 (d, J=8.0 Hz, 1H), 7.85 (d, J=7.6 Hz, 1H), 7.79 (d, J=7.6 Hz, 1H), 7.45 (m, 6H), 4.40 (m, 2H), 4.16 (s, 2H), 2.93 (m, 2H), 2.61 (s, 3H), 2.54 (m, 2H); MS (AP/CI): 441.3 (M+H)+.

Example 7j

N-{cis-3-[4-(2-Naphthalen-1-yl-acetylamino)-imidazol-1-yl]-cyclobutyl}-isobutyramide The title compound was prepared analogously to Example 7a; 1H NMR (400 MHz, CD3OD) δ 8.01 (d, J=7.9 Hz, 1H), 7.84 (d, J=7.5 Hz, 1H), 7.78 (d, J=7.5 Hz, 1H), 7.45 (m, 6H), 4.35 (m, 1H), 4.15 (s, 2H), 4.11 (m, 2H), 2.84 (m, 2H), 2.35 (m, 1H), 2.28 (m, 2H), 1.06 (d, J=6.6 Hz, 6H); MS (AP/CI): 391.1 (M+H)+.

Example 7k

6-Chloro-pyridine-2-carboxylic acid {cis-3-[4-(2-naphthalen-1-yl-acetylamino)-imidazol-1-yl]-cyclobutyl}-amide The title compound was prepared analogously to Example 7a; 1H NMR (400 MHz, CD3OD) δ 8.07 (d, J=7.9 Hz, 1H), 8.03 (d, J=7.5 Hz, 1H), 7.94 (m, 1H), 7.87 (d, J=7.9 Hz, 1H), 7.81 (d, J=7.9 Hz, 1H), 7.61 (d, J=7.1 Hz, 1H), 7.58 (s, 1H), 7.5 (m, 5H), 4.45 (m, 1H), 4.39 (m, 1H), 4.18 (s, 2H), 2.89 (m, 2H), 2.63 (m, 2H); MS (AP/CI): 460.2, 462.2 (M+H)+.

Example 8

Acylation of N-[1-(cis-3-amino-cyclobutyl)-1H-imidazol-4-yl]-2-naphthalen-1-yl-acetamide (Example 6) with various carboxylic acids and subsequent purification was carried out according to the following procedure: To the carboxylic acid (RCO₂H, 1 equiv, 0.075 mmol) in 1 dram screw cap vials was added a solution of N-[1-(cis-3-amino-cyclobutyl)-1H-imidazol-4-yl]-2-naphthalen-1-yl-acetamide (0.33 equiv, 8 mg, 0.025 mmol) in methylene chloride (1 mL). Next, PS-carbodiimide (Argonaut Technologies, 0.5 equiv, 39 mg, 0.038 mmol, 1 mmol/g) was added. The mixtures were shaken at 23° C. for 24 h. Note: If the acid was insoluble in methylene chloride, N,N-dimethylformamide (0.5 mL) was added. Each reaction mixture was transferred with methylene chloride (0.5 mL) to a 3 mL SPE cartridge (20 micron frit) with a tared 2 dram vial to collect solvent. The solvent was forced through the frit and the polymer was washed with THF (0.5 mL), methylene chloride (0.5 mL), THF (0.5 mL), and methylene chloride (0.5 mL). The solutions were concentrated under a stream of nitrogen and the crude products were analyzed by LCMS (Column: 3.9×150 mm Waters Symmetry $C_{18}$, 5 uM; flow=1.0 ml/min; solvent system: A=0.1% aqueous TFA; B=acetonitrile; linear gradient of 10–100% B over 10 min). If the desired parent ion (M+H) was observed, the crude reaction mixture was purified by preparative HPLC (Column: 30×150 mm Waters Symmetry $C_{18}$ 5 uM; flow=20 mL/min; solvent system: A=0.1% aqueous TFA;

B=acetonitrile; linear gradient of 0–100% B over 15 min) with the appropriate fractions determined by an in-line mass spectrometer. The purity of the chromatographed compound was determined by analytic HPLC (Column: 2.1×150 mm Waters Symmetry $C_{18}$ 5 uM; Flow: 0.5 mL/min; solvent system: A=0.1% aqueous TFA; B=acetonitrile; linear gradient of 0–100% B over 10 min) using UV: 254 nM and diode array for detection.

The following compounds were prepared by the above-described method. Their mass spectral data and chromatographic retention times are listed in Table 1:

Example 8a

Quinoline-2-carboxylic acid {cis-3-[4-(2-naphthalen-1-yl-acetylamino)-imidazol-1-yl]-cyclobutyl}-amide Example 8b 1H-Pyrrole-2-carboxylic acid {cis-3-[4-(2-naphthalen-1-yl-acetylamino)-imidazol-1-yl]-cyclobutyl}-amide Example 8c N-{cis-3-[4-(2-Naphthalen-1-yl-acetylamino)-imidazol-1-yl]-cyclobutyl}-2-m-tolyl-acetamide Example 8d Pyridine-2-carboxylic acid {cis-3-[4-(2-naphthalen-1-yl-acetylamino)-imidazol-1-yl]-cyclobutyl}-amide Example 8e 2-(3-Hydroxy-phenyl)-N-{cis-3-[4-(2-naphthalen-1-yl-acetylamino)-imidazol-1-yl]-cyclobutyl}-acetamide

TABLE 1

Acylated Products, Associated Retention Times, and Mass Spectral Data

| Example | Analytical HPLC (min) | LCMS (min) | (M + H) |
|---|---|---|---|
| 8a | 7.68 | 8.79 | 476.2 |
| 8b | 6.97 | 7.96 | 414.2 |
| 8c | 7.45 | 8.56 | 453.2 |
| 8d | 6.84 | 6.68 | 426.2 |
| 8e | 6.75 | 7.77 | 455.2 |

Column header: Retention Times

Preparation 5

4-{3-[4-(2-Naphthalen-1-yl-acetylamino)-imidazol-1-yl]-cyclobutylcarbamoyl}-piperidine-1-carboxylic acid 9H-fluoren-9-ylmethyl Ester Step 1

4-Piperidine carboxylic acid (129 mg, 1 mmol) was treated with sodium hydroxide (80 mg, 2 mmol) in water/dioxane (1:1, 10 mL). After 30 min of stirring at room temperature, 9-fluorenylmethyl chloroformate (259 mg, 1 mmol) in dioxane (2 mL) was added dropwise and then the reaction solution was stirred for 4 h. The solvent was removed in vacuo and was diluted with water. The pH was adjusted to 1 with HCl (1 N) and the aqueous solution was extracted with ethyl acetate. The organic layer was dried ($MgSO_4$), filtered, and concentrated in vacuo. Purification by silica gel chromatography (50:1:0.5 chloroform-methanol-acetic acid) afforded 340 mg (97% yield) of N-1-(fluorenylmethyloxycarbonyl)-4-piperidinylcarboxylic acid; 1H NMR (400 MHz, $CDCl_3$) d 7.75 (d, J=7.1 Hz, 2H), 7.55 (d, J=7.5 Hz, 2H), 7.39 (m, 2H), 7.30 (m, 2H), 4.4 (brs, 2H), 4.23 (t, J=6.5 Hz, 1H), 3.9 (brd, 2H), 2.9 (brs, 2H), 2.52 (m, 1H), 1.90 (brs, 2H), 1.62 (brs, 2H); MS (AP/CI): 352.0 (M+H)+.

Step 2

A solution of N-1-(fluorenylmethyloxycarbonyl)-4-piperidinylcarboxylic acid (Preparation 5, Step 1; 77 mg) in methylene chloride was treated with 1-(3-dimethylaminopropyl)-3-ethylcarbodiimide hydrochloride (84 mg) and DMAP (5 mg). After stirring for 30 min, N-[1-(cis-3-aminocyclobutyl)-1 H-imidazol4-yl]-2-naphthalen-1-yl-acetamide (Example 6), was added. The resulting mixture was then stirred for 4 h. Water was added, the solution was made neutral, and was extracted with ethyl acetate. The organic layer was dried ($MgSO_4$), filtered, and concentrated in vacuo. Purification by silica gel chromatography (20:1 chloroform-methanol) gave 101 mg (77% yield) of 4-{3-[4-(2-Naphthalen-1-yl-acetylamino)-imidazol-1-yl]-cyclobutyl-carbamoyl}-piperidine-1-carboxylic acid 9H-fluoren-9-ylmethyl ester; 1H NMR (400 MHz, CD3OD) δ 8.0 (d, J=8.3 Hz, 1H), 7.83 (m, 1H), 7.78 (dd, J=2.07, 7.5 Hz, 1H), 7.73 (d, J=7.5 Hz, 2H), 7.53 (d, J=6.6 Hz, 2H), 7.44 (m, 5H), 7.35 (m, 3H), 7.27 (m, 2H), 4.4 (brs, 2H), 4.2 (m, 1H), 4.15 (m, 5H), 2.85 (m, 4H), 2.25 (m, 3H), 1.7 (brs, 2H), 1.5 (brs, 2H); MS (AP/CI): 654.8 (M+H)+.

Example 9

Piperidine-4-carboxylic acid {cis-3-[4-(2-naphthalen-1-yl-acetylamino)-imidazol-1-yl]-cyclobutyl}-amide hydrochloride 4-{3-[4-(2-Naphthalen-1-yl-acetylamino)-imidazol-1-yl]-cyclobutylcarbamoyl}-piperidine-1-carboxylic acid 9H-fluoren-9-ylmethyl ester (Preparation 5, 100 mg, 0.15 mmol) in DMF (5 mL) was treated with piperidine (0.5 mL) and stirred at room temperature for 2 h. The solvent was removed in vacuo and the residue was purified by silica gel chromatography (4:1:0.08 chloroform-methanol-ammonium hydroxide) to afford the free base. The free base was dissolved in diethyl ether and treated with 1N HCl in methanol to afford the HCl salt (64 mg, 91% yield), piperidine-4-carboxylic acid {cis-3-[4-(2-naphthalen-1-yl-acetylamino)-imidazol-1-yl]-cyclobutyl}-amide hydrochloride; 1H NMR (400 MHz, CD3OD) δ 8.01 (d, J=8.0 Hz, 1H), 7.84 (d, J=8.2 Hz, 1H), 7.78 (d, J=7.8 Hz, 1H), 7.43 (m, 4H), 7.36 (s, 2H), 4.34 (m, 1H), 4.15 (s, 2H), 4.10 (m, 1H), 3.03 (m, 2H), 2.83 (m, 2H), 2.54 (m, 2H), 2.24 (m, 3H), 1.69 (m, 2H), 1.55 (m, 2H); MS (AP/CI): 432 (M+H)+.

Preparation 6

Isoquinolin-5-yl-acetic acid

Step 1

5-Aminoisoquinoline (5.0 g, 34.7 mmol) was mixed with 48% aqueous HBr (65 mL) at −78° C. for 15 min. Sodium nitrite (3.1 g, 45 mmol) in water (6 mL) was then added dropwise. After stirring for 15 min at −78° C., the mixture was warmed to 0° C. Copper powder (0.3 g) was added very slowly to avoid excessive foaming. After addition was completed, the reaction vessel was fitted with a reflux condensor and the mixture was heated to 100° C. for 4 h. The mixture was poured onto ice (ca. 200 g) and was made basic (pH=10) with KOH. The aqueous mixture was extracted with ethyl acetate, the combined organic layers were washed with brine, were dried ($MgSO_4$), were filtered, and were concentrated in vacuo. Purification by silica gel chromatography (10:1 hexanes-ethyl acetate) afforded 3.8 g (53% yield) of 5-bromoisoquinoline; 1H NMR (400 MHz, CD3OD) δ 9.25 (s, 1H), 8.57 (d, J=6.2 Hz, 1H), 8.1 (m, 3H), 7.60 (m, 1H); MS (AP/CI): 208.0, 210.0 (M+H)+.

Step 2

5-Bromoisoquinoline (Preparation 6, Step 1, 1.04 g, 5.0 mmol) was mixed with allyltributyltin (1.7 mL, 5.5 mmol) and dichloropalladium bis(triphenylphosphine) (176 mg, 0.25 mmol) in toluene (20 mL) under a nitrogen atmosphere. The mixture was heated at reflux for 16 h. After cooling to room temperature, a saturated aqueous solution of potassium fluoride (20 mL) was added with stirring, resulting in the formation of a precipitate. Following 15 min of stirring, the mixture was filtered and the organic layer was separated from the aqueous layer, was concentrated in vacuo and was purified by silica gel chromatography (6:1 hexanes-ethyl acetate) to give 778 mg (92% yield) of 5-allylisoquinoline; 1H NMR (400 MHz, $CDCl_3$) δ 9.25 (s, 1H), 8.54 (d, J=5.8 Hz, 1H), 7.85 (m, 1H), 7.79 (d, J=5.8 Hz, 1H), 7.56 (m, 2H), 6.1 (m, 1H), 5.15 (m, 1H), 5.05 (m, 1H), 3.81 (d, J=6.2 Hz, 2H); MS (AP/CI): 170.1 (M+H)+.

Step 3

5-Allylisoquinoline (Preparation 6, Step 2; 169 mg, 1.0 mmol) in methylene chloride (2 mL), acetic acid (0.5 mL), and water (0.5 mL) was treated with dimethyl polyethylene glycol (Mn ca. 500, 95 uL, 100 mg, 0.2 mmol) in methylene chloride (1 mL) at 23° C. The mixture was cooled to 0° C. and powdered $KMnO_4$ (521 mg, 3.3 mmol) was added portionwise, maintaining the temperature below 30° C. Following vigorous stirring for 18 h, the solvent was removed in vacuo and methanolic hydrogen chloride (10 mL, 1N) was added, and the mixture was refluxed for 4 h. The methanol was removed in vacuo, the residue was diluted with water, and the mixture was made basic with $Na_2CO_3$ (pH=9). The mixture was extracted with ethyl acetate, the resulting organic layer was washed with brine, was dried ($MgSO_4$), was filtered, was concentrated in vacuo, and was purified by silica gel chromatography (2:1 hexanes-ethyl acetate) to afford isoquinolin-5-yl-acetic acid methyl ester; 1H NMR (400 MHz, $CDCl_3$) δ 9.28 (brs, 1H), 8.58 (d, J=6.2 Hz, 1H), 7.95 (d, J=7.9 Hz, 1H), 7.80 (d, J=5.8 Hz, 1H), 7.66 (d, J=5.8 Hz, 1H), 7.59 (t, J=7.6 Hz, 1H), 4.06 (s, 2H), 3.70 (s, 3H); MS (AP/CI): 202.1 (M+H)+. Note: An impurity of 5-isoquinolylcarboxaldehyde was present following silica gel chromatography (ca. 20%).

Step 4

Isoquinolin-5-yl-acetic acid methyl ester (Preparation 6, Step 3; 90 mg, 0.448 mmol) was treated with aqueous sodium hydroxide (4N, 3 mL) and the solution was heated at 50° C. for 4 h. The solution was cooled to 0° C. and acetic acid (2 mL) was added dropwise, which resulted in the formation of a precipitate. The mixture was kept at 0° C. overnight (ca. 15 h) and the precipitate was removed via filtration and was washed with water. The solid was dried in air to afford 35 mg (47% yield) of isoquinolin-5-yl-acetic acid; 1H NMR (400 MHz, CD3OD) δ 9.24 (s, 1H), 8.47 (d, J=6.2 Hz, 1H), 8.04 (d, J=7.9 Hz, 1H), 7.96 (d, J=6.2 Hz, 1H), 7.74 (d, J=6.6 Hz, 1H), 7.66 (t, J=7.6 Hz, 1H), 4.11 (s, 2H); MS (AP/CI): 188.3 (M+H)+.

Preparation 7

N-[cis-3-(4-Nitro-imidazol-1H-yl)cyclobutyl]acetamide

Step 1 trans-Toluene-4-sulfonic acid 3-(4-nitro-imidazol-1-yl)-cyclobutyl ester (Preparation 1, Step 2; 3.6 g, 10.7 mmol) was mixed with sodium azide (7 g, 107 mmol) in ethanol (100 mL), water (35 mL), and chloroform (20 mL). The mixture was heated at reflux for 24 h. The ethanol and chloroform were removed in vacuo and resulting mixture was diluted with water and was extracted with ethyl acetate. The organic layer was washed with brine, was dried ($MgSO_4$), filtered, and concentrated in vacuo. Purification by silica gel chromatography (1:1 to 3:1 ethyl acetate-hexanes) gave 2.2 g (99%) of 1-(3-cis-azido-cyclobutyl)-4-nitro-1H-imidazole; 1H NMR (400 MHz, $CDCl_3$) δ 7.85 (s, 1H), 7.49 (s, 1H), 4.42 (m, 1H), 3.91 (m, 1H), 3.07 (m, 2H), 2.43 (m, 1H); MS (AP/CI): 208.5 (M+H)+.

Step 2

1-(3-cis-Azido-cyclobutyl)-4-nitro-1H-imidazole (Preparation 7, Step 1; 2.2 g, 10.7 mmol) in THF (100 mL) was treated with triphenylphosphine (3.36 g, 12.8 mmol) and water (10 mL). The solution was stirred at room temperature for 18 h. The solvent was removed in vacuo and the residue was purified by silica gel chromatography (20:1:0.4 chloroform-methanol-ammonium hydroxide) to give 1.95 g (100% yield) of 1-(3-cis-amino-cyclobutyl)-4-nitro-1H-imidazole; 1H NMR (400 MHz, CD3OD) δ 8.32 (s, 1H), 7.81 (s, 1H), 4.46 (m, 1H), 3.29 (m, 1H), 2.87 (m, 2H), 2.17 (m, 2H); MS (AP/CI): 183.1 (M+H)+.

Step 3

1-(3-cis-amino-cyclobutyl)-4-nitro-1H-imidazole (Preparation 7, Step 2; 500 mg, 2.75 mmol) was coupled with acetic acid and purified as in Example 7 to afford 594 mg (96% yield) of N-[cis-3-(4-nitro-imidazol-1H-yl)cyclobutyl]acetamide; 1H NMR (400 MHz, CD3OD) δ 8.30 (s, 1H), 7.82 (s, 1H), 4.58 (m, 1H), 4.17 (m, 1H), 2.95 (m, 2H), 2.39 (m, 2H), 1.93 (s, 3H); MS (AP/CI): 225.1 (M+H)+.

Preparation 8

N-[cis-3-(4-Nitro-imidazol-1-yl)-cyclobutyl]-benzamide

N-[cis-3-(4-Nitro-imidazol-1-yl)-cyclobutyl]-benzamide was prepared analogously to the product of Preparation 7; 1H NMR (400 MHz, CD3OD) δ 8.36 (s, 1H), 7.85 (m, 3H), 7.55 (m, 1H), 7.47 (m, 2H), 4.65 (m, 1H), 4.44 (m, 1H), 3.05 (m, 2H), 2.60 (m, 2H); MS (AP/CI): 287.3 (M+H)+.

Preparation 9

Pyridine-2-carboxylic acid [cis-3-(4-nitro-imidazol-1-yl)-cyclobutyl]-amide

Pyridine-2-carboxylic acid [cis-3-(4-nitro-imidazol-1-yl)-cyclobutyl]-amide was prepared analogously to the product of Preparation 7; 1H NMR (400 MHz, $CDCl_3$): δ 8.55 (m, 1H), 8.35 (d, J=7.0 Hz, 1H), 8.19 (d, J=7.9 Hz, 1H), 8.01 (s, 1H), 7.88 (td, J=1.65, 7.9 Hz; 1H), 7.57 (s, 1H), 7.47 (m, 1H), 4.5 (m, 2H), 3.17 (m, 2H), 2.72 (m, 2H); MS (AP/CI): 288.1 (M+H)+.

Example 9a

N-[1-(cis-3-acetylamino-cyclobutyl)-1H-imidazol-4-yl]-2-naphthalen-2-yl-acetamide N-[cis-3-(4-Nitro-imidazol-1H-yl)cyclobutyl]acetamide (Preparation 7; 50 mg, 0.22 mmol) was hydrogenated and acylated with 2-naphthyl acetic acid as in Example 1 to afford 35 mg (44% yield) of N-[1-(cis-3-acetylamino-cyclobutyl)-1H-imidazol-4-yl]-2-naphthalen-2-yl-acetamide; 1H NMR (400 MHz, CD3OD) δ 8.05 (d, J=8.0 Hz, 1H), 7.87 (d, J=7.6 Hz, 1H), 7.81 (d, J=6.4 Hz, 1H), 7.46 (m, 5H), 7.37 (s, 1H), 4.41 (m, 1H), 4.17 (s, 2H), 4.12 (m, 1H), 2.84 (m, 2H), 2.27 (m, 2H), 1.89 (s, 3H); MS (AP/CI): 363.3 (M+H)+.

Example 9b

N-{cis-3-[4-(2-lsoquinolin-5-yl-acetylamino)-imidazol-1-yl]-cyclobutyl}-benzamide The title compound was prepared analogously to Example 9a, using Preparation 8 and isoquinolin-5-yl acetic acid (Preparation 6); 1H NMR (400 MHz, CD3OD) δ 9.24 (s, 1H), 8.45 (d, J=6.2 Hz, 1H), 8.05 (d, J=7.9 Hz, 1H), 8.02 (J=6.2 Hz, 1H), 7.82 (m, 3H), 7.67 (m, 1H), 7.52 (m, 2H), 7.45 (m, 3H), 4.5 (m, 1H), 4.4 (m, 1H), 4.21 (s, 2H), 2.95 (m, 2H), 2.50 (m, 2H); MS (AP/CI): 426.3 (M+H)$^+$.

Example 9c

Pyridine-2-carboxylic acid {cis-3-[4-(2-isoquinolin-5-yl-acetylamino)-imidazol-1-yl]-cyclobutyl}-amide The title compound was prepared analogously to Example 9a, using Preparation 9 and isoquinolin-5-yl acetic acid (Preparation 6); 1H NMR (400 MHz, CD3OD) δ 9.23 (s, 1H), 8.60 (m, 1H), 8.44 (d, J=5.8 Hz, 1H), 8.03 (m, 3H), 7.92 (dt, J=1.7, 7.5 Hz, 1H), 7.78 (d, J=7.1 Hz, 1H), 7.66 (m, 1H), 7.58 (s, 1H), 7.5 (m, 1H), 7.46 (s, 1H), 4.45 (m, 1H), 4.40 (m, 1H), 4.20 (s, 2H), 2.85 (m, 2H), 2.6 (m, 2H); MS (AP/CI): 427.2 (M+H)+

Example 10

N-{cis-3-[4-(3-naphthalen-1-yl-ureido)-imidazol-1-yl]-cyclobutyl}-acetamide

N-[cis-3-(4-nitro-imidazol-1H-yl)cyclobutyl]acetamide (Preparation 7, 50 mg, 0.22 mmol) was reacted with phenyl chloroformate as described in Example 4. This afforded an inseparable mixture of mono- and bis-phenyl carbamate products following silica gel chromatography (20:1:0.2 chloroform-methanol-ammonium hydroxide) that were dissolved in 1:1 DMF/dioxane (500 uL). 1-Naphthylamine (31 mg, 0.22 mmol) was added and the mixture was heated at 70° C. for 16 h. Purification twice by silica gel chromatography (20:1:0.02 chloroform-methanol-ammonium hydroxide) gave 4.4 mg (5% yield) of N-{cis-3-[4-(3-naphthalen-1-yl-ureido)-imidazol-1-yl]-cyclobutyl}-acetamide; 1H NMR (400 MHz, CD3OD) δ 8.06 (d, J=8.0 Hz, 1H), 7.97 (d, J=8.8 Hz, 1H), 7.83 (d, J=7.6 Hz, 1H), 7.66 (d, J=8.4 Hz, 1H), 7.51 (m, 4H), 7.16 (s, 1H), 4.46 (m, 1H), 4.15 (m, 1H), 2.89 (m, 2H), 2.33 (m, 2H), 1.92 (s, 3H); MS (AP/CI): 364.0 (M+H)+.

What is claimed is:

1. A compound of the formula

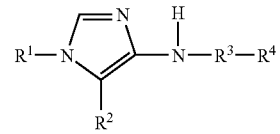

wherein $R^1$ is a $(C_3-C_8)$cycloalkyl, non-aromatic $(C_4-C_8)$ cycloalkenyl, $(C_5-C_{11})$bicycloalkyl or $(C_7-C_{11})$bicycloalkenyl,; and wherein $R^1$ is optionally substituted with from one to six substituents $R^5$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$S(=O)_2R^7$, —$S(=O)_2NR^7R^8$, —O—$S(=O)_2R^7$, —$N_3$, and $R^7$;

$R^2$ is H, F, —$CH_3$, —CN, or —$C(=O)OR^7$;

$R^3$ is —$C(=O)(CR^{10}R^{11})_n$;

$R^4$ is $(C_3-C_8)$cycloalkyl, $(C_4-C_8)$cycloalkenyl, $(C_5-C_{11})$bicycloalkyl, $(C_7-C_{11})$bicycloalkenyl, or $(C_6-C_{14})$;

and wherein $R^4$ is optionally substituted with from one to three substitutents $R^6$ independently selected from F, Cl, Br, I, nitro, cyano, —$CF_3$, —$NR^7R^8$, —$NR^7C(=O)R^8$, —$NR^7C(=O)OR^8$, —$NR^7C(=O)NR^8R^9$, —$NR^7S(=O)_2R^8$, —$NR^7S(=O)_2NR^8R^9$, —$OR^7$, —$OC(=O)R^7$, —$OC(=O)OR^7$, —$C(=O)OR^7$, —$C(=O)R^7$, —$C(=O)NR^7R^8$, —$OC(=O)NR^7R^8$, —$OC(=O)SR^7$, —$SR^7$, —$S(=O)R^7$, —$(=O)_2R^7$, —$S(=O)_2NR^7R^8$, or $R^7$;

each $R^7$, $R^8$, and $R^9$ is independently selected from H, straight chain or branched $(C_1-C_8)$alkyl, straight chain or branched $(C_2-C_8)$alkenyl, straight chain or branched $(C_2-C_8$ alkynyl), $(C_3-C_8)$cycloalkyl, $(C_4-C_8)$cycloalkenyl, $(C_5-C_{11})$bicycloalkyl, $(C_7-C_{11})$bicycloalkenyl, -and $(C_6-C_{14})$aryl, -wherein $R^7$, $R^8$, and $R^9$ are each independently optionally substituted with from one to six substituents independently selected from F, Cl, Br, I, $NO_2$, —CN, —$CF_3$, —$NR^{10}R^{11}$, —$NR^{10}C(=O)OR^{11}$, —$NR^{10}C(=O)NR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, —$OC(=O)R^{10}$, —$OC(=O)OR^{10}$, —$OC(=O)NR^{10}R^{11}$, —$OC(=O)SR^{10}$, —$SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}R^{11}$, and $R^{10}$;

each $R^{10}$, $R^{11}$, and $R^{12}$ is independently selected from H, straight chain or branched $(C_1-C_8)$alkyl, straight chain or branched $(C_2-C_8)$alkenyl, straight chain or branched $(C_2-C_8$ alkynyl), $(C_3-C_8)$cycloalkyl, $(C_4-C_8)$cycloalkenyl, $(C_5-C_{11})$bicycloalkyl, $(C_7-C_{11})$bicycloalkenyl, -and $(C^6-C_{14})$aryl, wherein $R^{10}$, $R^{11}$, and $R^{12}$ are each independently optionally substituted with from one to six substituents independently selected from F, Cl, Br, I, —$NO_2$, —CN, —$CF_3$, —$NR^{13}R^{14}$, —$NR^{13}C(=O)R^{14}$, —$NR^{13}(=O)OR^{14}$, —$NR^{13}C(=O)NR^{14}R^{15}$, —$NR^{13}S(=O)_2R^{14}$, —$NR^{13}S(=O)_2NR^{14}R^{15}$, —$OR^{13}$, —$OC(=O)R^{13}$, —$OC(=O)OR^{13}$, —$OC(=O)NR^{13}R^{14}$, —$OC(=O)SR^{13}$, —$SR^{13}$, —$S(=O)R^{13}$, —$S(=O)_2R^{13}$, —$S(=O)_2NR^{13}R^{14}$, —$C(=O)R^{13}$, —$C(=O)OR^{13}$, —$C(=O)NR^{13}R^{14}$, and $R^{13}$;

each $R^{13}$, $R^{14}$, and $R^{15}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, ($C_5$–$C_{11}$)bicycloalkyl, ($C_7$–$C_{11}$)bicycloalkenyl, -and ($C_6$–$C_{14}$)aryl wherein $R^{13}$, $R^{14}$, and $R^{15}$ are each independently optionally substituted with from one to six substituents independently selected from F, Cl, Br, I, —$NO_2$, —CN, —$CF_3$, —$NR^{16}R^{17}$, —$NR^{16}C(=O)R^{17}$, —$NR^{16}C(=O)OR^{17}$, —$NR^{16}C(=O)NR^{17}R^{18}$, —$NR^{16}S(=O)_2R^{17}$, —$NR^{16}S(=O)_2NR^{17}R^{18}$, —$OR^{16}$, —$OC(=O)R^{16}$, —$OC(=O)OR^{16}$, —$OC(=O)NR^{16}R^{17}$, —$OC(=O)SR^{16}$, —$SR^{16}$, —$S(=O)R^{16}$, —$S(=O)_2R^{16}$, —$S(=O)_2NR^{16}R^{17}$, —$C(=O)R^{16}$, —$C(=O)OR^{16}$, —$C(=O)NR^{16}R^{17}$, and $R^{16}$;

each $R^{16}$, $R^{17}$, and $R^{18}$ is independently selected from H, straight chain or branched ($C_1$–$C_8$)alkyl, straight chain or branched ($C_2$–$C_8$)alkenyl, straight chain or branched ($C_2$–$C_8$ alkynyl), ($C_3$–$C_8$)cycloalkyl, ($C_4$–$C_8$)cycloalkenyl, ($C_5$–$C_{11}$)bicycloalkyl, ($C_7$–$C_{11}$)bicycloalkenyl, and ($C_6$–$C_{14}$)aryl;

n is 0, 1, 2 or 3;

wherein $R^{10}$ and $R^{11}$ in —$C(=O)(CR^{10}R^{11})_n$- are for each iteration of n defined independently as recited above;

or a pharmaceutically acceptable salt thereof.

2. A compound according to claim 1, wherein $R^{10}$ and $R^{11}$ are, at each iteration of n, both hydrogen.

3. A compound according to claim 1, wherein $R^1$ is optionally substituted ($C_3$–$C_8$)cycloalkyl or optionally substituted ($C_5$–$C_{11}$) bicycloalkyl.

4. A compound according to claim 3, wherein $R^1$ is cyclopropyl, cyclobutyl, cyclopentyl, cyclohexyl, or norbornyl, each optionally substituted.

5. A compound according to claim 4, wherein $R^1$ is optionally substituted with from one to three substituents independently selected from F, Cl, Br, I, nitro, cyano, —$CF_3$, —$NR^7R^8$, —$NR^7C(=O)R^8$, —$OR^7$, —$C(=O)OR^7$, —$C(=O)R^7$, and $R^7$.

6. A compound according to claim 3, wherein $R^1$ is substituted with $NR^7C(=O)R^8$ and ($C_6$–$C_{14}$)aryl, and wherein said aryl, is optionally substituted with from one to six substituents independently selected from F, Cl, Br, I, —$NO_2$, —CN, —$CF_3$, —$NR^{10}R^{11}$, —$NR^{10}C(=O)R^{11}$, —$NR^{10}C(=O)OR^{11}$, —$NR^{10}C(=O)NR^{11}R^{12}$, —$NR^{10}S(=O)_2R^{11}$, —$NR^{10}S(=O)_2NR^{11}R^{12}$, —$OR^{10}$, —$OC(=O)R^{10}$, —$OC(=O)OR^{10}$, —$OC(=O)NR^{10}R^{11}$, —$OC(=O)SR^{10}$, —$SR^{10}$, —$S(=O)R^{10}$, —$S(=O)_2R^{10}$, —$S(=O)_2NR^{10}R^{11}$, —$C(=O)R^{10}$, —$C(=O)OR^{10}$, —$C(=O)NR^{10}R^{11}$, and $R^{10}$.

7. A compound according to claim 3, wherein $R^1$ is optionally substituted bicyclo-[3.1.0]-hexyl.

8. A compound of claim 1, wherein $R^4$ is an optionally substituted ($C_6$–$C_4$) aryl.

9. A compound according to claim 8, wherein $R^4$ is substituted phenyl.

10. A compound according to claim 8, wherein $R^4$ is optionally substituted naphthyl.

11. A compound according to claim 1, wherein $R^4$ is unsubstituted.

12. A compound according to claim 1, wherein $R^2$ is hydrogen.

13. A compound of claim 1, selected from the group consisting of:

N(1-cyclopentyl-1H-imidazol-4-yl)-2-(4methoxy-phenyl)-acetamide;

(1-cyclobutyl-1H-imidazol-4-yl)-carbamic acid phenyl ester;

N-[1-(cis-3-amino-cyclobutyl)-1H-imidazol-4-yl]-2-naphthalen-1-yl-acetamide;

N-{cis-3-[4-(2-naphthalen-1-yl-acetylamino)-imidazol-1-yl]-cyclobutyl)}-benzamide;

N-{cis-3-[4-(2-naphthalen-1-yl-acetylamino)-imidazol-1-yl]-cyclobutyl}-isobutyramide;

N-{cis-3-[4-(2-naphthalen-1-yl-acetylamino)-imidazol-1-yl]-cyclobutyl}-2-m-tolyl-acetamide;

2-(3-hydroxy-phenyl)-N-{cis-3-[4-(2-naphthalen-1-yl-acetylamino)-imidazol-1-yl]-cyclobutyl)}-acetamide;

N-[1-(cis-3-acetylamino-cyclobutyl)-1H-imidazol-4-yl]-2-naphthalen-2-yl-acetamide; and pharmaceutically acceptable salts of the foregoing compounds.

* * * * *